US009708637B2

(12) United States Patent
Shakulov et al.

(10) Patent No.: US 9,708,637 B2
(45) Date of Patent: Jul. 18, 2017

(54) METHOD FOR PRODUCING LOWER ALKYL ESTER

(71) Applicant: AJINOMOTO CO., INC., Tokyo (JP)

(72) Inventors: Rustem Saidovich Shakulov, Moscow (RU); Elena Vitalievna Klyachko, Moscow (RU); Vera Georgievna Doroshenko, Moscow (RU); Larisa Gotlibovna Airikh, Moscow region (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/164,381

(22) Filed: May 25, 2016

(65) Prior Publication Data
US 2016/0265019 A1    Sep. 15, 2016

Related U.S. Application Data

(62) Division of application No. 12/238,704, filed on Sep. 26, 2008, now Pat. No. 9,376,695.

(30) Foreign Application Priority Data

Sep. 27, 2007   (RU) .................... 2007135818

(51) Int. Cl.
| C12P 13/24 | (2006.01) |
| C12P 21/02 | (2006.01) |
| C12P 13/20 | (2006.01) |
| C12P 13/22 | (2006.01) |
| C12N 9/02 | (2006.01) |
| C12N 9/90 | (2006.01) |
| C12N 9/92 | (2006.01) |

(52) U.S. Cl.
CPC .............. *C12P 21/02* (2013.01); *C12N 9/001* (2013.01); *C12N 9/90* (2013.01); *C12N 9/92* (2013.01); *C12P 13/20* (2013.01); *C12P 13/222* (2013.01); *C12P 13/24* (2013.01); *C12Y 103/01013* (2013.01); *C12Y 503/01009* (2013.01); *C12Y 504/99005* (2013.01); *Y02P 20/52* (2015.11)

(58) Field of Classification Search
None
See application file for complete search history.

(56) References Cited

U.S. PATENT DOCUMENTS

| 4,278,765 | A |   | 7/1981  | Debabov et al. |
| 4,346,170 | A |   | 8/1982  | Sano et al. |
| 5,661,012 | A |   | 8/1997  | Sano et al. |
| 6,040,160 | A |   | 3/2000  | Kojima et al. |
| 6,287,569 | B1 | * | 9/2001  | Kipps ................ A61K 39/0005 424/199.1 |
| 6,589,741 | B2 |   | 7/2003  | Plückthun et al. |
| 6,960,455 | B2 |   | 11/2005 | Livshits et al. |
| 7,179,623 | B2 |   | 2/2007  | Livshits et al. |
| 7,259,003 | B2 |   | 8/2007  | Livshits et al. |
| 7,300,786 | B2 |   | 11/2007 | Klyachko et al. |
| 7,399,618 | B2 |   | 7/2008  | Klyachko et al. |
| 7,771,976 | B2 |   | 8/2010  | Gulevich et al. |
| 8,071,339 | B2 |   | 12/2011 | Klyachko et al. |
| 8,114,639 | B2 |   | 2/2012  | Filippov et al. |
| 8,394,612 | B2 |   | 3/2013  | Imaizumi et al. |
| 9,376,695 | B2 | * | 6/2016  | Shakulov ................ C12P 13/20 |
| 2001/0044139 | A1 |   | 11/2001 | Iomantas et al. |
| 2002/0182672 | A1 |   | 12/2002 | Kolkman |
| 2005/0048631 | A1 |   | 3/2005  | Klyachko et al. |
| 2005/0106688 | A1 |   | 5/2005  | Imaizumi et al. |
| 2005/0164356 | A1 |   | 7/2005  | Rieping et al. |
| 2005/0191684 | A1 |   | 9/2005  | Zimenkov et al. |
| 2005/0214911 | A1 |   | 9/2005  | Marchenko et al. |
| 2005/0277179 | A1 |   | 12/2005 | Takai et al. |
| 2006/0063240 | A1 |   | 3/2006  | Katashkina et al. |
| 2006/0088919 | A1 |   | 4/2006  | Rybak et al. |
| 2008/0153138 | A1 |   | 6/2008  | Livshits et al. |
| 2009/0137010 | A1 |   | 5/2009  | Shakulov et al. |

FOREIGN PATENT DOCUMENTS

| CN | 1373226 | 10/2002 |
| EP | 0488424 B1 | 3/1997 |
| EP | 1033407 A1 | 9/2000 |
| EP | 1087015 | 3/2001 |
| EP | 1239041 | 9/2002 |
| EP | 2003209 | 12/2008 |
| KR | 1020050044573 A | 5/2005 |
| KR | 1020060127990 A | 12/2006 |
| RU | 2202607 C2 | 4/2003 |
| WO | WO03/089605 A2 | 10/2003 |
| WO | WO2007/100009 | 9/2007 |

OTHER PUBLICATIONS

Corvaisier, S., et al., "Inhibition of Transfer Messenger RNA Aminoacylation and trans-Translation by Aminoglycoside Antibiotics," J. Biol. Chem. 2003;278(17):14788-14797.
Gottesman, S., et al., "The ClpXP and ClpAP proteases degrade proteins with carboxy-terminal peptide tail added by the SsrA-tagging system," Genes & Dev. 1998;12:1338-1347.
Hayes, C. S., et al., "Stop codons preceded by rare arginine codons are efficient determinants of SsrA tagging in *Escherichia coi*," PNAS 2002;99(6):3440-3445.
Jensen, P. R., et al., "The Sequence of Spacers between the Consensus Sequences Modulates the Strength of Prokaryotic Promoters," Appl. Environ. Microbiol. 1998;64(1):82-87.

(Continued)

*Primary Examiner* — Hope Robinson
(74) *Attorney, Agent, or Firm* — Shelly Guest Cermak; Cermak Nakajima & McGowan LLP

(57) ABSTRACT

A method for producing an L-amino acid is described, for example, L-phenylalanine and L-histidine, by fermentation using a bacterium of the Enterobacteriaceae family, wherein the bacterium has been modified by attaching a DNA fragment able to be transcribed encoding the peptide represented in SEQ ID NO: 2, or a variant thereof, particularly a portion of the ssrA gene, to the 3'-end of gene encoding for the bacterial enzyme, which influences on the L-amino acid biosynthesis, such as chorismate mutase/prephenate dehydrogenase or phosphoglucose isomerase.

12 Claims, 4 Drawing Sheets

(56) References Cited

OTHER PUBLICATIONS

Jensen, P. R., et al., "Artificial Promoters for Metabolic Optimization," Biotechnol. Bioeng. 1998;58(2-3):191-195.

Komine, Y., et al., "A tRNA-like structure is present in 10Sa RNA, a small stable RNA from *Escherichia coli*," Proc. Natl. Acad. Sci. USA 1994;91:9223-9227.

Schönhuber, W., et al., "Utilization of tmRNA sequences for bacterial identification," BMC Microbiol. 2001;1(1):20.

Tu, G-F., et al., "C-terminal Extension of Truncated Recombinant Proteins in *Escherichia coli* with a 10Sa RNA Decapeptide," J. Biol. Chem. 1995;270(16):9322-9326.

Ueda, K., et al., "Bacterial SsrA system plays a role in coping with unwanted translational readthrough caused by suppressor tRNAs," Genes to Cells 2002;7(5):509-519.

Yamamoto, Y., et al., "SsrA-mediated trans-translation plays a role in mRNA quality control by facilitating degradation of truncated mRNAs," RNA 2003;9:408-418.

Decision of Patent Grant issued on Oct. 5, 2011 in the corresponding Korean Patent App. No. 10-2008-0095229 with English translation thereof.

Lutke-Eversloh, T., et al., "Feedback Inhibition of Chorismate Mutase/Prephenate Dehydrogenase (TyrA) of *Escherichia coli*: Generation and Characterization of Tyrosine-Insensitive Mutants," Appled and Environ. Microbiol. 2005;71(11):7224-7228.

Neuenschwander, M., et al., "A simple selection strategy for evolving highly efficient enzymes," Nature Biotechnol. 2007;25(10):1145-1147.

Doroshenko, V. G., et al., "Construction of an L-phenylalanine-producing tyrosine-prototrophic *Escherichia coli* strain using tyrA ssrA-like tagged alleles," Biotechnol. Left. 2010;32:1117-1121.

Williams, G. J., et al., "Expanding the promiscuity of a natural-product glycosyltransferase by directed evolution," Nature Chem. Biol. 2007;3(10):657-662.

Xia, T., et al., "The aroQ-Encoded Monofunctional Chorismate Mutase (CM-F) Protein Is a Periplasmic Enzyme in Erwinia herbicola," J. Bacteriol. 1993;175(15):4729-4737.

Roche, E. D., et al., "Identification of Endogenous SsrA-tagged Proteins Reveals Tagging at Positions Corresponding to Stop Codons," J. Biol. Chem. 2001;276(30):28509-28515.

Karzai, A. W., et al., "The SsrA-SmpB system for protein tagging, directed degradation and ribosome rescue," Nat. Struct. Biol. 2000;7(6):449-455.

Roche, E. D., et al., "SsrA-mediated peptide tagging caused by rare codons and tRNA scarcity," The EMBO Journal 1999;18(16):4579-4589.

Preliminary Search Report for French Patent App. No. 0856540 (Feb. 13, 2013) with English translation thereof.

Third Office Action for Chinese Patent App. No. 200810149297.2 (Feb. 16, 2013) with English translation thereof.

Muto, A., et al., "Requirement of transfer-messenger RNA for the growth of Bacillus subtilis under stresses," Genes to Cells 2000;5:627-635.

Office Action for German Patent App. No. 102008049533.6 issued Mar. 21, 2017 with English language translation thereof.

\* cited by examiner

Fig.1. Scheme of gene *tyrA* extension.

Fig. 2. Relative positions of primers P1 and P2 on plasmid pMW118-attL-Cm-attR.

Fig. 3. Construction of chromosomal DNA fragment comprising inactivated *pheA* gene.

```
BACSU      GKTNSFNQN------VALAA
BACST      GK-----QN------YALAA
SERMA      AN----DEN------YALAA
ECOLI      AN----DEN------YALAA
PSEFL      AN----DETYGE--YALAA
PSECL      AN----DETYGE--YALAA
PSEUPU     AN----DETYGEETYALAA
             .:      :.       ****
```

METHOD FOR PRODUCING LOWER ALKYL ESTER

This application is a Divisional of, and claims priority under 35 U.S.C. §120 to, U.S. patent application Ser. No. 12/238,704, filed Sep. 26, 2008, now U.S. Pat. No. 9,376,695, and claims priority therethrough under 35 U.S.C. §119 to Russian patent application Ser. No. 2007135818 filed on Sep. 27, 2007, the entireties of which are incorporated by reference herein. Also, the Sequence Listing electronically herewith is hereby incorporated by reference (File Name: 2016-05-25T_US-347D_Seq_List; File Size: 34 KB; Date Created: May 25, 2016).

BACKGROUND OF THE INVENTION

Technical Field

The present invention relates to a method for producing an L-amino acid by fermentation, and more specifically to genes which aid in this fermentation. These genes are useful for improving L-amino acid production, particularly L-phenylalanine and L-histidine.

Background Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170, 5,661,012 and 6,040,160) and creating bacterial strains which are deficient in the genes which use the precursors of the target compound for other pathways, or creating bacterial strains which are deficient in the genes responsible for degradation of the target compound.

These manipulations usually result in strains which cannot grow, grow only at a significantly reduced rate, or require additional nutrients, such as amino acids. For example, enhancing the expression of some genes may become excessive and could lead to significant inhibition of bacterial growth and, as a result, lower the ability of the bacterium to produce the target compound.

A possible approach for avoiding the difficulties described above is to optimize the expression of the genes which encode proteins involved in the distribution of the carbon, nitrogen, or phosphorus fluxes, or the excretion of the target substance out of the bacterial cell.

This aim was often accomplished by introducing a mutation into a promoter sequence of the amino acid- or nucleic acid-biosynthesizing genes (European Patent Application EP1033407A1), by obtaining the library of synthetic promoters with different strengths (Jensen P. R., and Hammer K., Appl. Environ. Microbiol., 1998, 64, No. 1. 82-87 Biotechnol. Bioeng., 1998, 58, 2-3, 191-5), and creating a library of artificial promoters (PCT application WO03089605).

It is known that tagging a protein with the ssrA peptide tag, encoded by SsrA RNA, marks the tagged protein for proteolytic degradation (Gottesmann S. and al, Genes&Dev.,12:1338-1347 (1998)). SsrA RNA (Synonyms: SsrA, tmRNA, 10Sa RNA, transfer-messenger RNA, SipB, B2621) functions to release a stalled ribosome from the end of a "broken" mRNA that is missing a stop codon by acting both as a tRNA and as an mRNA, using a "trans-translation" mechanism. SsrA also mediates the release of the stalled ribosome due to lack of an appropriate tRNA (Hayes C. S. and al, PNAS, 99(6):3440-3445 (2002)). Other translation problems can also lead to SsrA activity. In addition, SsrA RNA stimulates degradation of defective mRNAs (Yamamoto Y. et al, RNA, 9:408-418 (2003)).

The SsrA RNA contains a tRNA-like structural region that is processed by RNase P and charged by alanyl-tRNA synthetase (Komine Y et al, Proc. Natl. Acad. Sci. USA, 91 (20):9223-7 (1994)). The SsrA RNA also has a region that acts as a messenger RNA and encodes a translated tag that is added to the nascent protein and which targets this protein for degradation (Tu G.-F.and al, J Biol Chem, 270(16):9322-9326 (1995)). The structure of the SsrA RNA and the translational mechanism have been examined in detail (Corvaisier S. et al, J Biol Chem, 278(17):14788-97 (2003)). The SsrA RNA is transcribed as a larger precursor RNA that is then processed to form the mature RNA.

SsrA is similar to RNAs from *Mycoplasma capricolum, Bacillus subtilis* (Muta A., et al., Genes to Cells, 5:627-635 (2000)), *Dichelobacter nodosus, Synechococcus* sp. strains PCC6301 and PCC6803, *Thermus thermophilus, Salmonella enterica* serovar *Typhimurium*, and to a two-piece RNA from *Caulobacter crescentus*. The tmRNA genes have been used as probes for the identification of bacterial species (Schonhuber W. and al, BMC Microbiology, 1(1):20 (2001)).

However, there have been no reports describing the use of ssrA-tagging for L-amino acid production, for example, L-phenylalanine or L-histidine production. Particularly, there is no previous description of using a bacterium of the Enterobacteriaceae family containing a DNA encoding the peptide of SEQ ID NO: 2 or a variant thereof, attached immediately downstream of a gene encoding a bacterial enzyme which influences L-amino acid biosynthesis.

SUMMARY OF THE INVENTION

Figure 1:
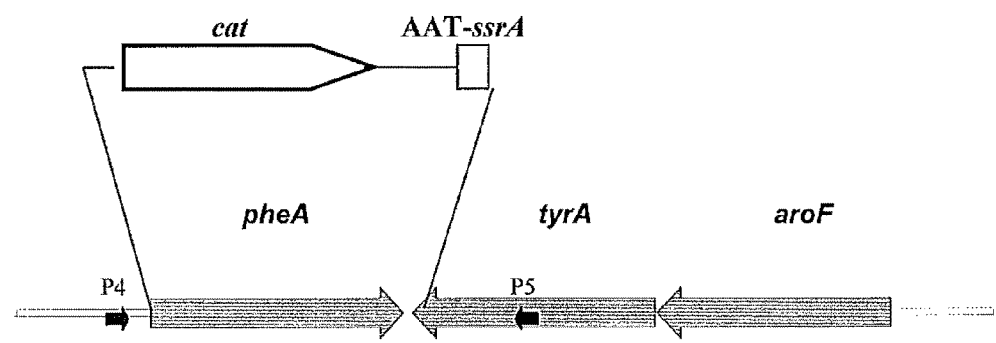
FIG. 1 shows the scheme for tyrA gene extension.

Aspects of the present invention include enhancing the productivity of L-amino acid-producing strains and a method for producing L-amino acids using these strains. The above aspects were achieved by finding that SsrA-tagging of an enzyme involved in the synthesis of a target amino acid that shares common steps in its biosynthesis pathway with other amino acids can enhance production of the target amino acid at the expense of the amino acids having common biosynthesis steps and/or precursors. It was also found that SsrA-tagging of an enzyme involved in the distribution of the carbon fluxes between different pathways of glycolysis (for example the pentose phosphate and Entner-Duodoroff pathways) can enhance production of those amino acids with precursors produced in one of the pathways of glycolysis. In either case, it was found that the prototrophic properties of the modified bacteria are maintained.

This aim was achieved by constructing a new variant tyrA gene and a new variant pgi gene, wherein the resulting proteins both have a C-terminal short peptide sequence encoded by part of ssrA gene. It was shown that the use of this mutant TyrA-ssrA could enhance L-phenylalanine production when the mutant tyrA-ssrA gene is introduced into the cells of the L-phenylalanine-producing strain in place of the native tyrA gene. It also was shown that the use of such mutant Pgi-ssrA could enhance L-histidine production when the mutant pgi-ssrA gene is introduced into the cells of the L-histidine-producing strain in place of the native pgi gene. Thus, the present invention has been completed.

It is an aspect of the present invention to provide an L-amino acid producing bacterium of the Enterobacteriaceae family comprising a DNA comprising a gene encoding a bacterial enzyme which influences L-amino acid biosynthesis, and a DNA fragment able to be transcribed and encoding the peptide of SEQ ID NO: 2, or a variant thereof, wherein said DNA fragment is attached to said gene at the 3' end of said gene.

It is a further aspect of the present invention to provide the bacterium described above, wherein said bacterium belongs to the genus *Escherichia*.

It is a further aspect of the present invention to provide the bacterium described above, wherein said bacterium is an L-phenylalanine producing bacterium.

It is a further aspect of the present invention to provide the bacterium described above, wherein the enzyme is chorismate mutase/prephenate dehydrogenase.

It is a further aspect of the present invention to provide the bacterium described above, wherein said bacterium is an L-histidine producing bacterium.

It is a further aspect of the present invention to provide the bacterium described above, wherein the enzyme is phosphoglucose isomerase.

It is a further aspect of the present invention to provide a method for producing an L-amino acid comprising cultivating the bacterium described above in a culture medium, and isolating the L-amino acid from the culture medium.

It is a further aspect of the present invention to provide the method described above, wherein said L-amino acid is L-phenylalanine.

It is a further aspect of the present invention to provide the method described above, wherein said L-amino acid is L-histidine.

It is a further aspect of the present invention to provide a method for producing a lower alkyl ester of α-L-aspartyl-L-phenylalanine, comprising cultivating the bacterium described above in a culture medium to produce and accumulate L-phenylalanine in the medium, and synthesizing the lower alkyl ester of α-L-aspartyl-L-phenylalanine from the aspartic acid or a derivative thereof and the obtained L-phenylalanine.

It is a further aspect of the present invention to provide the method described above, wherein the method further comprising esterifying L-phenylalanine to generate a lower alkyl ester of L-phenylalanine, condensing the lower alkyl ester of L-phenylalanine with the aspartic acid derivative, wherein the derivative is N-acyl-L-aspartic anhydride, separating the lower alkyl ester of N-acyl-α-L-aspartyl-L-phenylalanine from the reaction mixture, and hydrogenating the lower alkyl ester of N-acyl-α-L-aspartyl-L-phenylalanine to generate the lower alkyl ester of α-L-aspartyl-L-phenylalanine.

DETAILED DESCRIPTION OF THE PREFERRED EMBODIMENTS

1. Bacterium of the Present Invention

It is known that some L-amino acids have common precursors during biosynthesis by a cell, such as aromatic amino acids, branched chain amino acids, etc. When producing such an amino acid in a bacterial strain, it is useful to make the strain auxotrophic for the other amino acids which have a common precursor with the targeted amino acid. This can prevent the common precursor from directing the biosynthesis away from the biosynthetic pathway of the targeted amino acid.

Another method for ensuring production of the targeted amino acid, as opposed to those having a common precursor, is to generate a so called "leaky"mutation in an enzyme which is responsible for producing the other amino acids from the common precursor. In this case, it is not necessary to feed the bacterium with the other L-amino acid(s), since synthesis of these L-amino acids in the bacterium is suppressed.

SsrA-tagging of an enzyme results in a reduction in the enzyme activity, since the enzyme is degraded by the transcribed ssrA-tagged RNA via RNase P (Komine Y et al, Proc. Natl. Acad. Sci. USA, 91 (20):9223-7 (1994)) and proteolysis of the ssrA-tagged enzyme by ClpXP and ClpAP proteases (Wah D. A. et al, Chem. Biol., 9(11):1237-45 (2002)). Such modification by ssrA-tagging permits retention of the prototrophic properties of the modified bacterium, while exhibiting a leaky-type phenotype. Also, the ssrA-tagging permits the reduction of the level of by-products by decreasing the activity of one or several enzymes involved in the biosyntesis of such by-products.

"L-amino acid-producing bacterium" means a bacterium which has an ability to cause accumulation of an L-amino acid in a medium when the bacterium is cultured in the medium. The L-amino acid-producing ability may be imparted or enhanced by breeding. The phrase "L-amino acid-producing bacterium" as used herein also means a bacterium which is able to produce and cause accumulation of an L-amino acid in a culture medium in an amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L of the target L-amino acid. The term "L-amino acids" includes L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. L-histidine is particularly preferred. Aromatic amino acid, such as L-phenylalanine, L-tryptophan and L-tyrosine is more preferred and L-phenylalanine is particularly preferred.

The Enterobacteriaceae family includes bacteria belonging to the genera *Escherichia, Enterobacter, Erwvinia, Klebsiella, Pantoea, Providencia, Salmonella, Serratia, Shigella, Morganella*, etc. Specifically, those classified into the Enterobacteriaceae according to the taxonomy used in the NCBI (National Center for Biotechnology Information) database (www.ncbi.nlm.nih.gov/htbinpost/Taxonomy/wgetorg?mode=Tree&id=1236&lvl=3&keep=1&srchmode=1&unlock) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* is not particularly limited; however, for example, bacteria described by Neidhardt, F. C. et al. (*Escherichia coli* and *Salmonella typhimurium*, American Society for Microbiology, Washington D.C., 1208, Table 1) are encompassed.

The bacterium encompasses a strain of the Enterobacteriaceae family which has an ability to produce an L-amino acid and has been modified by attaching a DNA fragment having part of the ssrA gene to the 3'-end of a gene encoding a bacterial enzyme. The part of the ssrA gene encodes for the peptide represented in SEQ ID NO: 2 or a variant thereof, and the bacterial enzyme is involved in the biosynthetic pathway of an L-amino acid which has a common precursor with the targeted L-amino acid. In addition, the bacterium encompasses a strain of the Enterobacteriaceae family which has an ability to produce an L-amino acid and has been transformed with a DNA fragment encoding part of the ssrA gene so that components of the peptide encoded by the DNA fragment are expressed.

The ssrA gene (synonyms: ECK2617, b2621, sipB) encodes the tmRNA (synonyms: SsrA, 10Sa RNA, transfer-messenger RNA, SipB, B2621). The ssrA gene (nucleotides from 2753615 to 2753977 in the sequence of GenBank accession NC_000913.2, gi: 49175990) is located between the smpB and intA genes on the chromosome of *E. coli* K-12. The ssrA gene from *Escherichia coli* is represented by SEQ ID NO: 1. The sequence of the tmRNA-encoded proteolysis-inducing peptide tag is represented by SEQ ID NO: 2. This peptide is encoded by nucleotides on positions from 90 to 119 of gene ssrA represented in SEQ ID NO: 1. Other ssrA genes have also been elucidated as follows: tmRNA-encoded proteolysis-inducing peptide tag from *Bacillus subtilis, Bacillus stearothermophilus, Serratia marcescens, Escherichia coli, Pseudomonas flurescens, Pseudomonas chlororaphis*, and *Pseudomonas putida*.

Bacteria which are able to concurrently produce two L-amino acids which have a common precursor may be used. The goal of the present invention was achieved by using a strain which had been previously modified to concurrently produce two amino acids, namely L-phenylalanine and L-tyrosine. Such a strain can be obtained by destroying the transcriptional dual regulator, namely, the tyrR gene by the standard Red-driven recombination method. Deletion of the tyrR gene can be confirmed by PCR using the chromosomal DNA of the transformed strain as a template. Bacteria which are able to produce L-amino acids may be used, and preferably bacteria which are able to concurrently produce phenylalanine and tyrosine *E. coli* MG1655 ΔtyrR is an example of such a strain. *E. coli* strain MG1655 ΔtyrR was obtained by substitution of the chromosomal tyrR gene with a DNA cassette containing the Cm marker followed by excision of the marker using standard techniques described in WO 05/010175. Also, an L-histidine producing strain in which the pgi gene is modified by ssrA-tagging to increase flux of D-glucose-6-phosphate to the pentose phosphate pathway to enhance productivity of L-histidine is also encompassed and described.

The phrase "a DNA fragment able to be transcribed and encoding the peptide of SEQ ID NO: 2 or a variant thereof, wherein said fragment is attached to said gene at the 3' end of said gene" means that the gene encoding the bacterial enzyme has been modified to have additional nucleotide residues on its 3'-end as compared to a non-modified gene, for example, a gene of the wild-type strain. The presence of this DNA fragment (SEQ ID NO: 2 or a variant thereof) at the 3'-end of the gene encoding the bacterial enzyme leads to the formation of a tagged mRNA species, and the translated corresponding protein has an additional peptide tagged, or attached to, the C-terminus thereof. The bacterial enzyme may be modified by methods that include genetic recombining, C-terminal extensions, C-terminal fusions, and so forth. The length of the modified enzyme protein can be measured, for example, by Western blot with specific antibodies, protein sequencing, and the like. The phrase "attaching the DNA fragment encoding the peptide of SEQ ID NO: 2 or a variant thereof to the carboxyl terminus of the protein" can also mean that the translated modified protein is expressed in the bacterium in such a way that the modified protein is degraded at a controllable rate (McGinness K. E. and al, Molecular Cell, 22: 701-707 (2006)).

The phrase "a DNA fragment able to be transcribed" means that the DNA fragment is attached to the 3'-end of the gene coding for the bacterial enzyme in such way that the stop-codon of the gene encoding the bacterial enzyme is removed and the necessary DNA fragment is introduced immediately after the last codon of the gene. Such a DNA construct is transcribed as one transcriptional unit tagging the desired DNA fragment to the mRNA of the gene of interest (the bacterial enzyme). It also results in expression of ssrA-tagged proteins.

The phrase "a variant thereof" means a peptide which has changes in the sequence, whether they are deletions, insertions, additions, or substitutions of amino acids, but still maintains the desired activity at a useful level, for example, useful for decreasing the activity of tagged protein and consequently enhancing production of an L-amino acid. The number of changes in the variant peptide depends on the position or the type of amino acid residues in the primary structure of the peptide. The number of changes may be 1 to 4 and preferably 1 to 2 for the peptide listed as SEQ ID NO: 2. These changes in the variants can occur in regions of the peptide which are not critical for the function of the peptide. This is because some amino acids have high homology to one another so the activity is not affected by such a change. Therefore, the peptide variants may have a homology of not less than 70%, preferably not less than 80%, and more preferably not less than 90%, and most preferably not less than 95% with respect to the entire amino acid sequences shown in SEQ ID NO: 2 as long as the ssrA-tagged protein is recognized by proteases resulting in subsequent degradation. Homology between two amino acid sequences can be determined using the well-known methods, for example, the computer program BLAST 2.0, which calculates three parameters: score, identity and similarity.

The substitution, deletion, insertion, or addition of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Figures 4, 5:
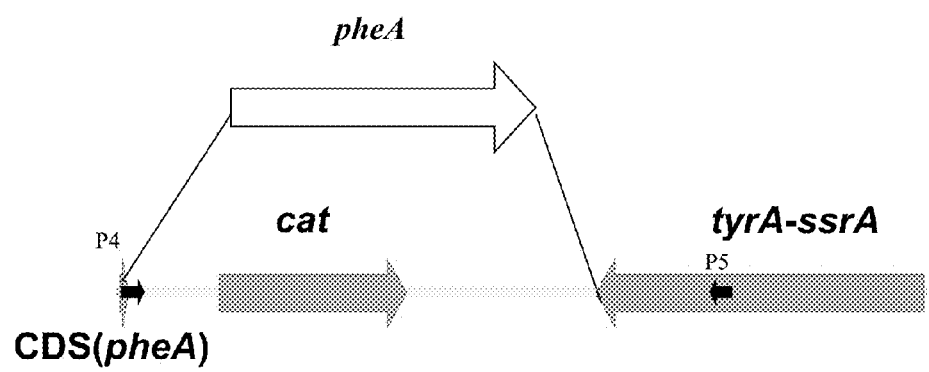
FIG. 4 shows the scheme for replacing the cat gene locus with the pheA gene and the *E. coli* chromosome locus containing tyrA-ssrA allele and cat gene. The P4 and P5 sites were used to check the construction.
FIG. 5 shows the alignment of the primary sequences of the tmRNA-encoded proteolysis-inducing peptide tag from *Bacillus subtilis* (BACSU—SEQ ID NO: 23), *Bacillus stearothermophilus* (BACST—SEQ ID NO: 24), *Serratia marcescens* (SERMA—SEQ ID NO: 25), *Escherichia coli* (ECOLI—SEQ ID NO: 26), *Pseudomonas flurescens* (PSEFL—SEQ ID NO: 27), *Pseudomonas chlororaphis* (PSECL—SEQ ID NO: 28), *Pseudomonas putida* (PSEUPU—SEQ ID NO: 29). The alignment was done by using the PIR Multiple Alignment program (pir.georgetown.edu). The identical amino acids are marked by an asterisk (*), similar amino acids are marked by a colon (:).

Data comparing the primary sequences of tmRNA-encoded proteolysis-inducing peptide tag from Bacillus subtilis (BACSU), Bacillus stearothermophilus (BACST), Serratia marcescens (SERMA), Escherichia coli (ECOLI), Pseudomonas flurescens (PSEFL), Pseudomonas chlororaphis (PSECL), Pseudomonas putida (PSEUPU) show a high level of homology of the amino acid sequence "YALAA" (SEQ ID NO: 2) in the C-terminus (see FIG. 5). It is possible to substitute similar (marked by colon) amino acids residues by the similar amino acid residues without deterioration of the peptide activity. But modifications of other non-conserved amino acid residues may not lead to alteration of the activity of tmRNA-encoded proteolysis-inducing peptide tag. Peptide tagged amino acid sequences referred to by McGinness K. E. et al.(Molecular Cell, 22:701-707 (2006)) can also be considered as a peptide variant.

The DNAs which encode substantially the same peptides as components of the tag peptide may be obtained, for example, by modifying the nucleotide sequences of DNAs encoding components of tag peptide (SEQ ID NO: 1), for example, by means of the site-directed mutagenesis method so that one or more amino acid residues at a specified site involve deletion, substitution, insertion, or addition. DNAs modified as described above may be obtained by conventionally known mutation treatments. Such treatments include hydroxylamine treatment of the DNA encoding proteins, or treatment of the bacterium containing the DNA with UV irradiation or a reagent such as N-methyl-N'-nitro-N-nitrosoguanidine or nitrous acid. DNAs encoding substantially the same peptides as tag peptide can be obtained by expressing DNAs having a mutation as described above in an appropriate cell, and investigating the activity of the expressed product. DNAs encoding substantially the same peptide as tag peptide can also be obtained by isolating DNAs that are hybridizable with probes having nucleotide sequences which contain, for example, the nucleotide sequences shown in SEQ ID NO: 1 under the stringent conditions, and encode peptides having the activities of tag peptide. The "stringent conditions" referred to herein are conditions under which so-called specific hybrids are formed, and non-specific hybrids are not formed. For example, stringent conditions can be exemplified by conditions under which DNAs having high homology, for example, DNAs having homology of not less than 50%, preferably not less than 60%, more preferably not less than 70%, further preferably not less than 80%, and still more preferably not less than 90%, and most preferably not less than 95% are able to hybridize with each other, but DNAs having homology lower than the above are not able to hybridize with each other. Alternatively, stringent conditions may be exemplified by conditions under which DNA is able to hybridize at a salt concentration equivalent to ordinary washing conditions in Southern hybridization, i.e., 1×SSC, 0.1% SDS, preferably 0.1×SSC, 0.1% SDS, at 60° C. Duration of washing depends on the type of membrane used for blotting and, as a rule, what is recommended by the manufacturer. For example, recommended duration of washing, for example, for the Hybond™ N+ nylon membrane (Amersham), under stringent conditions approximately is 15 minutes. Preferably, washing may be performed 2 to 3 times.

Partial sequences of the nucleotide sequence of SEQ ID NO: 1 can also be used as probes. Probes may be prepared by PCR using primers based on the nucleotide sequence of SEQ ID NO: 1 and DNA fragments containing the nucleotide sequence of SEQ ID NO: 1 as templates.

The substitution, deletion, insertion, or addition of nucleotides as described above also includes mutations which naturally occur (mutant or variant), for example, due to variety in the species or genus of bacterium, which contains the components of tag peptide.

Expression of a bacterial gene which has a DNA fragment encoding the peptide represented in SEQ ID NO: 2, or a variant thereof, attached to the 3'-end of the gene can be achieved by transforming a bacterium with the DNA encoding the peptide, and more exactly, by introducing the DNA fragment into the bacterial chromosome downstream of the gene encoding the protein without disturbing the coding frame, or preferably, by replacing the native chromosomal gene with a mutant gene encoding the tagged protein by conventional methods. Transformation of a bacterium with DNA will result in the formation of a new chromosomal mutant gene encoding the elongated protein. Methods of transformation include any known methods that have hitherto been reported.

For example, the following methods may be employed to introduce the DNA encoding the mutant gene by gene recombination. A mutant gene is prepared, and the bacterium is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). To increase the permeability of the cells to the DNA, treating the recipient cells with calcium chloride has been reported for Escherichia coli K-12 (Mandel, M. and Higa, A., J. Mol. Biol., 53, 159 (1970)) and may be used.

Methods for preparation of plasmid DNA include, but are not limited to, digestion and ligation of DNA, transformation, selection of an oligonucleotide as a primer and the like, or other methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

In the present invention, the phrase "bacterial enzyme which influences L-amino acid biosynthesis" means an enzyme involved in the biosynthetic pathway of the undesired product, for example, the product which shares a common precursor with the targeted L-amino acid. The phrase "bacterial enzyme involved in the biosynthetic pathway of the undesired product" means an enzyme catalyzing the reaction of a common precursor of the targeted L-amino acid and the undesired product being converted into a the undesired product. This happens because the enzyme directs the reaction down the branch of the biosynthetic pathway which results in production of the undesired product. The phrase "bacterial enzyme which influences L-amino acid biosynthesis" also means an enzyme involved in the biosynthesis pathway of by-products of the targeted L-amino acid. The presence of such by-products can cause significant technical problems during purification, and negatively effect the L-amino acid production.

Genes encoding for the bacterial enzyme which influences L-amino acid biosynthesis are the genes of interest. Such genes are represented by, but not limited to, tyrA gene encoding for chorismate mutase/prephenate dehydrogenase, pgi gene encoding for phosphoglucose isomerase, ilvE gene encoding for branched-chain amino-acid aminotransferase, ilvA and tdcB genes encoding for threonine dehydratases, sdaA and sdaB genes encoding for L-threonine deaminases, argA gene encoding for N-acetylglutamate synthase, argG gene encoding for argininosuccinate synthase, proB gene encoding for γ-glutamyl kinase, thrB gene encoding for homoserine kinase, gene encoding for homoserine dehydrogenase etc. In general, any gene encoding an enzyme which causes the production of a metabolite resulting from deviation from the pathway of the target L-amino acid and/or involved in the formation of a by-product is the gene of interest.

Chorismate mutase/prephenate dehydrogenase (synonyms: B2600, TyrA) catalyzes reversible conversion between chorismate and prephenate, and reversible conversion between prephenate and p-hydroxyphenylpyruvate, which is the intermediate compound in the pathway biosynthesis of tyrosine. Chorismate conversion is the first step in the biosynthesis of both tyrosine and phenylalanine. Modification of the TyrA protein by ssrA-tagging can be useful for decreasing the flux of prephenate to the L-tyrosine biosynthetic pathway, and enhancing the production of L-phenylalanine. The activity of chorismate mutase/prephenate dehydrogenase can be measured by using a stopped-time assay in the presence of 2.5 mM chorismate or by immunodiffusion analysis of the enzyme-antibody complexes in plates prepared with 0.8% agarose (Rood J. I., Perrot B. et al., Eur J Biochem.; 124, 513-519 (1982)). The wild-type tyrA gene (synonyms: ECK2597, b2600) which encodes the chorismate mutase/prephenate dehydrogenase from Escherichia coli has been elucidated. The tyrA gene (nucleotides complementary to nucleotides 2736970 to 2738091 in the sequence of GenBank accession NC_000913.2, gi: 49175990) is located between the pheA and aroF genes on the chromosome of E. coli K-12. The tyrA gene from Escherichia coli is represented by SEQ ID NO: 3, and the amino acid sequence encoded by the tyrA gene is represented by SEQ ID NO: 4.

In the biosynthetic pathway of phenylalanine, reversible conversion between prephenate and phenylpyruvate is catalyzed by chorismate mutase/prephenate dehydratase (synonyms: B2599, PheA), which subunit is encoded by pheA gene (synonyms: ECK2596, b2599) in E. coli. The pheA gene (nucleotides from 2735767 to 2736927 in the sequence of GenBank accession NC_000913.2, gi: 49175990) is located between the pheA gene leader peptide and tyrA gene on the chromosome of E. coli K-12. The pheA gene from Escherichia coli is represented by SEQ ID NO: 5, and the amino acid sequence encoded by the pheA gene is represented by SEQ ID NO: 6. Simultaneous modification of the TyrA and PheA proteins by ssrA-tagging can be useful for decreasing the flux of chorismate to the L-tyrosine and L-tyrosine biosynthetic pathway and enhancing the production of L-phenylalanine.

Phosphoglucose isomerase (synonyms: B4025, Pgi, glucose-6-phosphate isomerase, D-glucose-6-phosphate-ketol-isomerase) catalyzes reversible conversion between β-D-glucose-6-phosphate and D-fructose-6-phosphate in gluconeogenesis, and glycolysis pathways. Decreasing phosphoglucose isomerase activity leads to the redistribution of carbon fluxes in favor of the pentose phosphate pathway in which histidine precursor metabolite 5-phosphoribosyl 1-pyrophosphate is generated. Activity of phosphoglucose isomerase can be detected by, for example, the method described in Friedberg I. (J Bacteriol., 112,3:1201-1205 (1972)) in a coupled assay by using G6P dehydrogenase (Winkler H. H., J Bacteriol.,101, 2:470-475 (1970)). The wild-type pgi gene (synonyms: ECK4017, b4025) which encodes the glucose-6-phosphate isomerase from Escherichia coli has been elucidated. The pgi gene (nucleotides from 4,231,781 to 4,233,430 in the sequence of GenBank accession NC_000913.2, gi: 49175990) is located between the lysC and yjbE genes on the chromosome of E. coli K-12. The pgi gene from Escherichia coli is represented by SEQ ID NO: 7, and the amino acid sequence encoded by the pgi gene is represented by SEQ ID NO: 8.

Branched-chain amino acid aminotransferase (synonyms: B3770, IlvE) catalyzes a series of transamination reactions, each of which generates α-ketoglutarate and one of three aliphatic branched chain amino acids. Modification of the IlvE protein by ssrA-tagging can be useful for decreasing the flux of 2-ketoisovalerate to the L-valine biosynthetic pathway, which also results in decreasing the amount of L-isoleucine as by-product and enhancing the production of L-leucine. The activity of branched-chain amino acid aminotransferase can be measured by the method described, for example, in Lee-Peng F C et al (J. Bacteriol., 139(2); 339-45 (1979)). The wild-type ilvE gene (synonyms: ECK3762, b3770, threonine deaminase, L-threonine hydrolyase) which encodes the branched chain amino acid aminotransferase from Escherichia coli has been elucidated. The ilvE gene (nucleotides 3,950,507 to 3,951,436 in the sequence of GenBank accession NC_000913.2, gi: 49175990) is located between the ilvM and ilvD genes on the chromosome of E. coli K-12.

Threonine dehydratase (synonyms: B3772, Ile, IlvA) catalyzes the deamination of L-threonine. Modification of the IlvA protein by ssrA-tagging can be useful for preventing L-theonine degradation and decreasing the flux of L-threonine to the L-isoleucine biosynthetic pathway, as well as being useful for L-arginine production. The activity of threonine dehydratase can be measured by the method described, for example, in Eisenstein, E. (J. Biol. Chem., 266(9); 5801-7 (1991)). The wild-type ilvA gene (synonyms: ECK3764, b3772, ile) which encodes the threonine dehydratase from Escherichia coli has been elucidated. The ilvA gene (nucleotides 3,953,354 to 3,954,898 in the sequence of GenBank accession NC_000913.2, gi: 49175990) is located between the ilvD and ilvY genes on the chromosome of E. coli K-12.

Threonine dehydratase (synonyms: B3117, Tdc, TdcB, threonine deaminase, L-serine dehydratase, serine deaminase, L-threonine hydrolyase) catalyzes deamination of L-threonine. Modification of the TdcB protein by ssrA-tagging can be useful for preventing L-theonine degradation and decreasing the flux of L-threonine to the L-isoleucine biosynthetic pathway. The wild-type tdcB gene (synonyms:

ECK3106, b3117, tdc) which encodes the threonine dehydratase from *Escherichia coli* has been elucidated. The tdcB gene (nucleotides complementary to nucleotides 3,263,061 to 3,264,050 in the sequence of GenBank accession NC_000913.2, gi: 49175990) is located between the tdcC and tdcA genes on the chromosome of *E. coli* K-12.

Threonine deaminases SdaA (synonyms: B1814, SdaA, SDH1, L-SD, L-threonine deaminase I, L-serine dehydratase 1, SDH-1, L-SD1, L-hydroxyaminoacid dehydratase 1, L-serine deaminase 1, L-serine hydro-lyase 1) and SdaB (synonyms: B2797, SdaB, L-threonine deaminase II, L-serine deaminase 2, L-serine dehydratase 2, SDH-2, L-SD2, L-serine hydrolyase 2) catalyze deamination of L-threonine. Modification of the threonine deaminase protein by ssrA-tagging can be useful for preventing L-theonine degradation and decreasing the flux of L-threonine to the L-isoleucine biosynthetic pathway. The wild-type sdaA gene (synonyms: ECK1812, b1814) and sdaB gene (synonyms: ECK2792, b2797) which encode the threonine deaminases from *Escherichia coli* have been elucidated. The sdaA gene (nucleotides 1,894,956 to 1,896,320 in the sequence of GenBank accession NC_000913.2, gi: 49175990) is located between the yeaB and yoaD genes on the chromosome of *E. coli* K-12. The sdaB gene (nucleotides 2,927,598 to 2,928,965 in the sequence of GenBank accession NC_000913.2, gi: 49175990) is located between the sdaC and xni genes on the chromosome of *E. coli* K-12.

N-acetylglutamate synthase (synonyms: B2818, ArgA, NAGS, acetyl-CoA:L-glutamate N-acetyltransferase, amino-acid-N-acetyltransferase) catalyzes the synthesis of N-acetylglutamate from L-glutamate and acetyl-CoA, which is the first step in the superpathway of arginine and ornithine biosynthesis. Modification of the ArgA protein by ssrA-tagging can be useful to accumulate glutamate for L-proline production. The activity of N-acetylglutamate synthase can be measured by the method described, for example, in Marvil, D. K. and Leisinger, T. (J. Biol. Chem., 252(10); 3295-303 (1977)). The wild-type argA gene (synonyms: ECK2814, Arg2, Argl, b2818) which encodes the N-acetylglutamate synthase from *Escherichia coli* has been elucidated. The argA gene (nucleotides 2,947,264 to 2,948,595 in the sequence of GenBank accession NC_000913.2, gi: 49175990) is located between the amiC and recD genes on the chromosome of *E. coli* K-12.

Argininosuccinate synthase (synonyms: B3172, ArgG, argininosuccinate synthetase, citrulline-aspartate ligase, L-citrulline:L-aspartate ligase) catalyzes the synthesis of argininosuccinate L-aspartate and citrulline. Modification of the ArgG protein by ssrA-tagging can be useful for citrulline production. The wild-type argG gene (synonyms: ECK3161, b3172) which encodes the argininosuccinate synthase from *Escherichia coli* has been elucidated. The argG gene (nucleotides 3,316,659 to 3,318,002 in the sequence of GenBank accession NC_000913.2, gi: 49175990) is located between the argR and yhbX genes on the chromosome of *E. coli* K-12.

γ-glutamyl kinase (synonyms: B0242, ProB, glutamate 5-kinase, GK, ATP:L-glutamate 5-phosphotransferase, G5K) catalyzes the reaction of glutamate phosphorylation, which is the first reaction in the synthesis of proline. Modification of the ProB protein by ssrA-tagging can be useful to accumulate glutamate for L-arginine production. The activity of γ-glutamyl kinase can be measured by the method described, for example, in Smith, C. J. et al, (J. Bacteriol., 157(2); 545-51 (1984)). The wild-type proB gene (synonyms: ECK0243, pro(2), b0242, pro2) which encodes the γ-glutamyl kinase from *Escherichia coli* has been elucidated. The proB gene (nucleotides 259,612 to 260,715 in the sequence of GenBank accession NC_000913.2, gi: 49175990) is located between the phoE and proA genes on the chromosome of *E. coli* K-12.

Homoserine kinase (synonyms: B0003, ThrB, ATP:L-homoserine O-phosphotransferase) catalyzes the reaction of homoserine phosphorylation. Modification of the ThrB protein by ssrA -tagging can be useful for L-methionine production. The activity of homoserine kinase can be measured by the method described, for example, in Shames, S. L. and Wedler, F. C. (Arch. Biochem. Biophys., 235(2); 359-70 (1984)). The wild-type thrB gene (synonyms: ECK0003, b0003) which encodes the homoserine kinase from *Escherichia coli* has been elucidated. The thrB gene (nucleotides 2,801 to 3,733 in the sequence of GenBank accession NC_000913.2, gi: 49175990) is located between the thrA and thrC genes on the chromosome of *E. coli* K-12.

Homoserine dehydrogenase catalyzes the reaction of the formation of L-aspartate-semialdehyde from homoserine. In *Escherichia coli*, the homoserine dehydrogenase is the part of aspartate kinase/homoserine dehydrogenase protein encoded by thrA gene. But in other microorganisms, such as Corynebacteria, homoserine dehydrogenase is a separate enzyme. Modification of the homoserine dehydrogenase by ssrA-tagging can be useful for L-lysine production.

The ssrA, tyrA, pheA, pgi, ilvE, ilvA, tdcB, sdaA, sdaB, argA, argG, proB, thrB, and other genes of interest can be obtained by PCR (polymerase chain reaction; refer to White, T. J. et al., *Trends Genet.*, 5, 185 (1989)) utilizing primers prepared based on the known nucleotide sequences of the genes. Genes encoding for tag peptides from other microorganisms can be obtained in a similar manner.

The above-described techniques and teachings for attaching a DNA fragment able to be transcribed encoding the peptide represented in SEQ ID NO: 2 or a variant thereof, to the 3'-end of the genes encoding chorismate mutase/prefenate dehydrogenase and phosphoglucose isomerase can be similarly applied to modify the activities of other proteins transcribed from other genes of interest.

The bacterium can be obtained by introducing the aforementioned DNAs into a bacterium which inherently have the ability to produce L-amino acids. Alternatively, the bacterium can be obtained by imparting the ability to produce L-amino acids to a bacterium which already contains the DNAs.

L-amino acid-producing Bacteria

Bacteria which are able to produce either aromatic or non-aromatic L-amino acids may be used in the present invention.

L-phenylalanine-producing Bacteria

Examples of parent strains for deriving L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as A J 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-histidine-producing Bacteria

Examples of parent strains for deriving L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116 -B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554), and the like.

Examples of parent strains for deriving L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI ), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-tryptophan-producing Bacteria

Examples of parent strains for deriving the L-tryptophan-producing bacteria include, but are not limited to, strains belonging to the genus *Escherichia*, such as *E. coli* JP4735/pMU3028 (DSM10122) and JP6015/pMU91 (DSM10123) which is deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parent strains for deriving the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of $\alpha$ and $\beta$ subunits which are encoded by the trpA and trpB genes, respectively. In addition, L-tryptophan-producing ability may be improved by enhancing expression of the isocitrate lyase-malate synthase operon (WO2005/103275).

L-valine-producing Bacteria

Example of parent strains for deriving L-valine-producing bacteria of, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, $1^{st}$ Dorozhny Proezd, 1) on Jun. 24, 1988 under accession number VKPM B-4411.

Furthermore, mutants requiring lipoic acid for growth and/or lacking $H^+$-ATPase can also be used as parent strains (WO96/06926).

L-isoleucine-producing Bacteria

Examples of parent strains for deriving L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

L-leucine-producing Bacteria

Examples of parent strains for deriving L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase which is not subject to feedback inhibition by L-leucine (U.S. Pat. No. 6,403,342). In addition, the bacterium may be improved by enhancing the expression of one or more genes coding for proteins which excrete L-amino acid from the bacterial cell. Examples of such genes include the b2682 and b2683 genes (ygaZH genes) (EP 1239041 A2).

L-arginine-producing Bacteria

Examples of parent strains for deriving L-arginine-producing bacteria include, but are not limited to, strains belonging to the genus Escherichia, such as E. coli strain 237 (VKPM B-7925) (U.S. Patent Application 2002/058315 A1) and its derivative strains harboring mutant N-acetylglutamate synthase (Russian Patent Application No. 2001112869), E. coli strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-citrulline-producing Bacteria

Examples of parent strains for deriving L-citrulline-producing bacteria include, but are not limited to, strains belonging to the genus Escherichia containing mutant feedback resistant carbamoylphosphate synthetase (U.S. Pat. No. 6,991,924) and the like.

2. Method of the Present Invention

The method of the present invention is a method for producing an L-amino acid by cultivating the bacterium in a culture medium to produce and excrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the used microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

Phenylalanine produced by the method may be used for, for example, producing the lower alkyl ester of α-L-aspartyl-L-phenylalanine (also referred to as "aspartame"). That is, the method includes production of the lower alkyl ester of α-L-aspartyl-L-phenylalanine by using L-phenylalanine as a raw material. The method includes synthesizing the lower alkyl ester of α-L-aspartyl-L-phenylalanine from L-phenylalanine produced by the method as described above and aspartic acid or its derivative. As a lower alkyl ester, methyl ester, ethyl ester and propyl ester, or the like can be mentioned.

The process for synthesizing the lower alkyl ester of α-L-aspartyl-L-phenylalanine from L-phenylalanine and aspartic acid or its derivative is not particularly limited and any conventional method can be applied so long as L-phenylalanine or its derivative can be used for synthesis of the lower alkyl ester of α-L-aspartyl-L-phenylalanine. Specifically, for example, the lower alkyl ester of α-L-aspartyl-L-phenylalanine may be produced by the following process (U.S. Pat. No. 3,786,039). L-phenylalanine is esterified to obtain the lower alkyl ester of L-phenylalanine. The L-phenylalanine alkyl ester is then reacted with L-aspartic acid derivative in which the amino group and .beta.carboxyl group are protected, and the a-carboxyl group is esterified to activate. The derivative includes N-acyl-L-aspartic anhydride such as N-formyl-, N-carbobenzoxy-, or N-p-methoxycarbobenzoxy-L-aspartic anhydride. By the condensation reaction, a mixture of N-acyl-α-L-aspartyl-L-phenylalanine and N-acyl-α-L-aspartyl-L-phenylalanine is obtained. If the condensation reaction is performed in the presence of an organic acid having an acid dissociation constant at 37° C. of 10-4 or less, the ratio of the α form to the β form in the mixture is increased (Japanese Patent Laid-Open Publication No. 51-113841). Then the N-acyl-α-L-aspartyl-L-phenylalanine separated from the mixture, followed by hydrogenation to obtain α-L-aspartyl-L-phenylalanine.

EXAMPLES

The present invention will be more concretely explained below with reference to the following non-limiting Examples.

Example 1

Construction of the E. coli strain MG1655ΔtyrRtyrA-ssrA, Which Contains the Mutant tyrA-ssrA Gene 1. Substitution of the Native pheA Gene and 36-nt Located at the 3' End of tyrA Gene Region, in E. coli with the Mutant tyrA-ssrA Gene.

To substitute the native pheA gene and 36-nt located at the 3' end of tyrA gene region, a DNA fragment carrying 1) the 36-nt located at the 5' end of pheA gene, 2) cat gene with attL and attR sites, 3) a DNA fragment encoding the chloramphenicol resistance marker ($Cm^R$), 4) the stop codon TAA, 5) the 30-nt located at positions from 90 to 119 of the ssrA gene, and 6) the 36-nt located at the 3' end of tyrA gene was integrated into the chromosome of *E. coli* MG1655 ΔtyrR in place of the native pheA gene and the 3'-end tyrA gene region by the method described by Datsenko K. A. and Wanner B. L. (Proc. Natl. Acad. Sci. USA, 2000, 97, 6640-6645) which is also called "Red-mediated integration" and/or "Red-driven integration" (FIG. 1).

This DNA fragment was obtained in two consecutive PCR runs where 5 μl of amplification products from the first PCR were used as a template for the second PCR.

Figure 2:
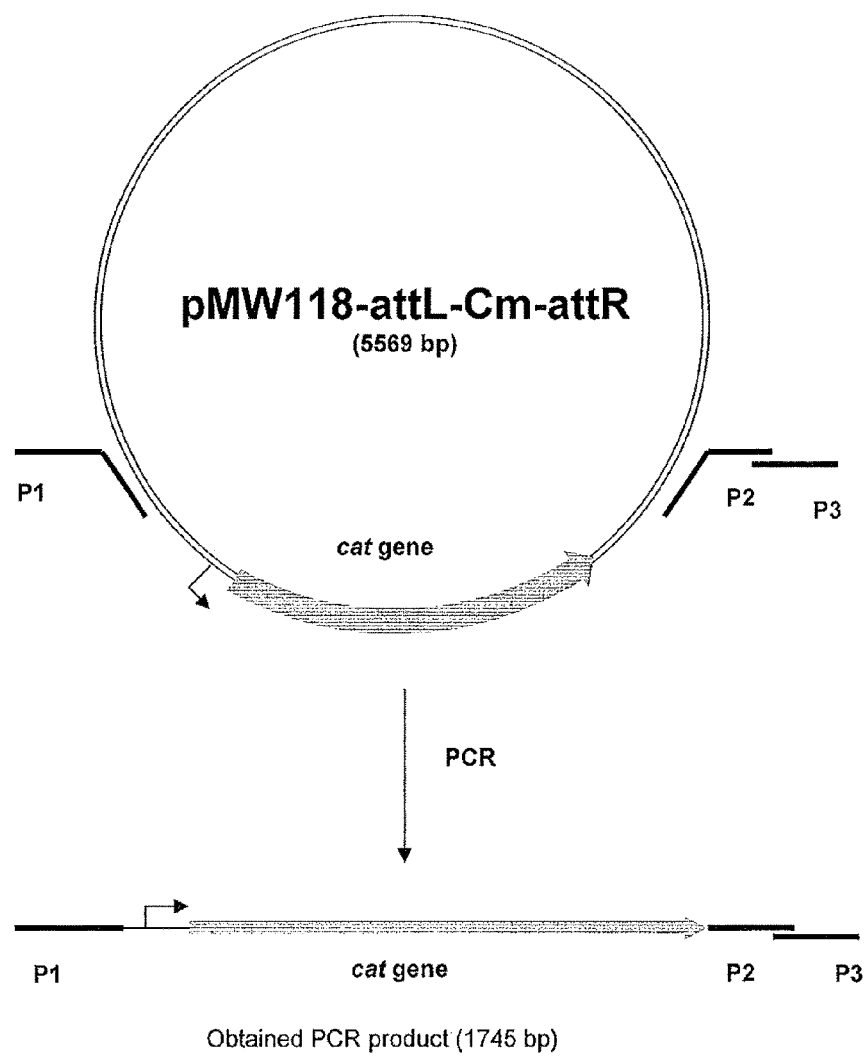
FIG. 2 shows the relative positions of primers P1 and P2 on plasmid pMW118-attL-Cm-attR.

The first DNA fragment containing the $Cm^R$ marker encoded by the cat gene was obtained by PCR using primers P1 (SEQ ID NO: 9) and P2(SEQ ID NO: 10) and plasmid pMW118-attL-Cm-attR as a template (WO 05/010175) (FIG. 2). Primer P1 contains both a region identical to the 36-nt region located at the 5' end of the pheA gene and a region complementary to the 27-nt attL region of pMW118-attL-Cm-attR. Primer P2 contains both a region identical to the 30-nt region of the ssrA gene and a region complementary to the 27-nt attR region of pMW118-attL-Cm-attR. Between these two regions, the stop codon TAA was inserted in primer P2. Conditions for PCR were as follows: denaturation for 5 min at 95° C.; profile for 30 cycles: 30 sec at 95° C., 30 sec at 50° C., 1 min at 72° C.; final step: 5 min at 72° C.

A 1709-bp PCR product was obtained and purified in agarose gel and 5 μl of this was used as a template for the second PCR reaction, using primers P1 (SEQ ID NO: 9) and P3 (SEQ ID NO: 11). Primer P3 contains both a region complementary to the 36-nt region located at the 3' end of the tyrA gene and a region identical to the 18-nt region located at the 5'-end of the primer P2. Conditions for PCR were as follows: denaturation for 5 min at 95° C.; profile for 30 cycles: 30 sec at 95° C., 30 sec at 50° C., 1 min at 72° C.; final step: 5 min at 72° C.

A 1745-bp PCR product was obtained and purified in agarose gel and was used for electroporation of the *E. coli* strain MG1655ΔtyrR, which contains the plasmid pKD46 which has a temperature-sensitive replication origin. The plasmid pKD46 (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of the *E. coli* strain MG1655ΔtyrR in the place of the native pheA gene and 36-nt located at the 3' end of tyrA gene region.

Electrocompetent cells were prepared as follows: *E. coli* MG1655ΔtyrR/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (10 mM) [arabinose was used to induce the plasmid encoding the Red system genes]. The cells were grown with aeration at 30° C. to an $OD_{600}$ of ≈0.6 and then were made electrocompetent by concentrating 100-fold and washing three times with ice-cold deionized $H_2O$. Electroporation was performed using 70 μl of cells and ≈100 ng of the PCR product. The electroporation was done using a "BioRad" electroporator (USA, No. 165-2098, version 2-89) according to the manufacturer's instructions. The shocked cells were diluted with 1 ml of SOC medium (Sambrook et al, "Molecular Cloning. A Laboratory Manual, Second Edition", Cold Spring Harbor Laboratory Press, 1989), incubated at 37° C. for 2 h, and then spread on L-agar containing chloramphenicol (20 μg/ml) and grown at 37° C. to select $Cm^R$ recombinants.

2. Verification of the pheA Gene Deletion by PCR

After 24 h of growth, colonies were tested for the presence of $Cm^R$ marker by PCR using locus-specific primers P4 (SEQ ID NO: 12) and P5 (SEQ ID NO: 13). For this purpose, a freshly isolated colony was suspended in water (20 μl) and 1 μl of the obtained suspension was used for PCR. The temperature profile was as follows: the initial DNA denaturation at 95° C. for 5 min; then 30 cycles (denaturation at 95° C. for 30 s, annealing at 50° C. for 30 s, and elongation at 72° C. for 1 min 10 sec), and a final elongation at 72° C. for 5 min.

Figure 3:
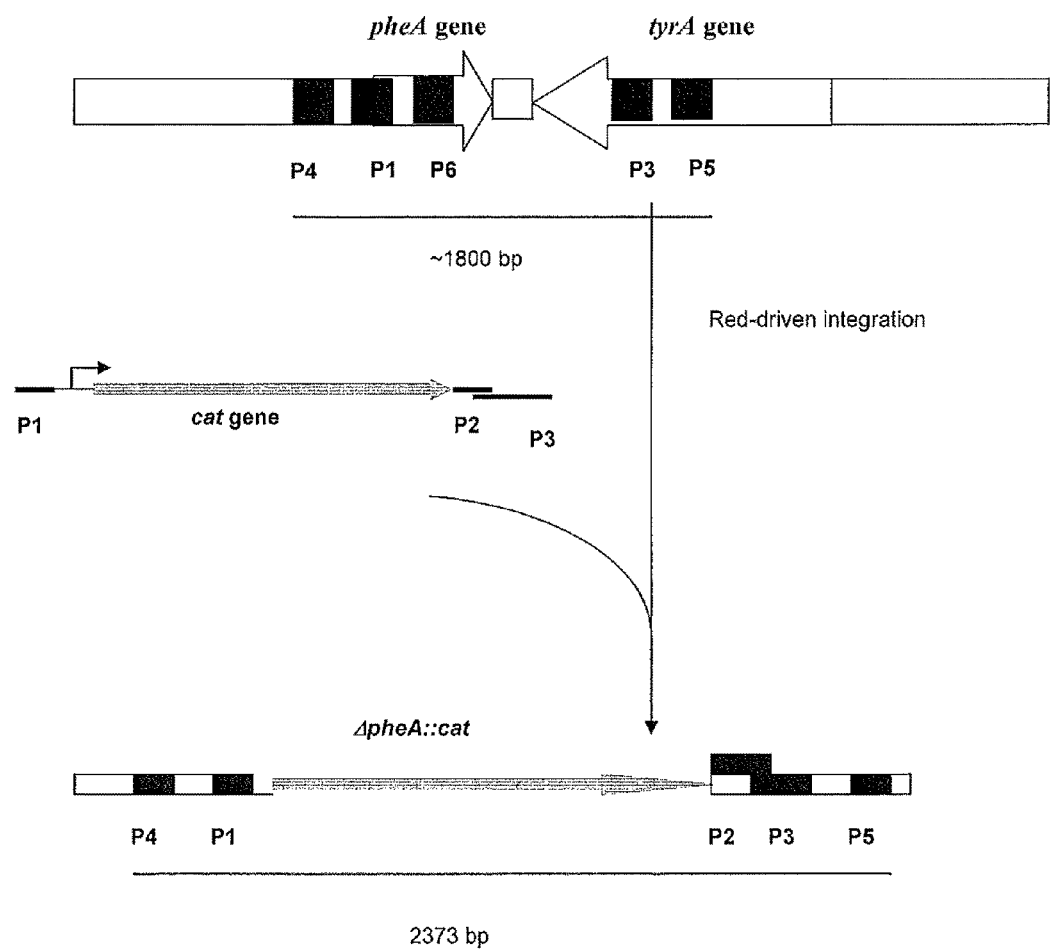
FIG. 3 shows the construction of the chromosomal DNA fragment with the deleted pheA gene.

A few of the $Cm^R$ colonies tested contained the required 2373-bp DNA fragment, confirming the substitution of the 1869-bp native region of the pheA gene by the hybrid tyrA-ssrA gene (see FIGS. 1 and 3). The resulting mutant strain was named MG1655 ΔtyrR ΔpheA::cat tyrA-ssrA.

3. Substitution of the Cat Gene in *E. coli* MG1655 ΔtyrR ΔpheA::cat tyrA-ssrA Strain with the Wild-Type pheA Gene.

To substitute the cat gene, a DNA fragment carrying the wild-type pheA gene was integrated into the chromosome of *E. coli* MG1655 ΔtyrR ΔpheA::cat tyrA-ssrA/pKD46 in place of the cat gene by the method described by Datsenko K. A. and Wanner B. L. (Proc. Natl. Acad. Sci. USA, 2000, 97, 6640-6645) which is also called "Red-mediated integration" and/or "Red-driven integration", and is also described in Example 1 (FIG. 3).

The wild-type pheA gene was obtained by PCR using the chromosomal DNA of *E. coli* MG1655 as the template, and primers P4 (SEQ ID NO: 12) and P6 (SEQ ID NO: 14).

Primer P6 contains both a 30-nt region identical to the region located at positions from 90 to 119 of the ssrA gene having the stop codon TAA and a region complementary to the 19-nt region located at the 3' end of the pheA gene.

Conditions for PCR were as follows: denaturation for 5 min at 95° C.; profile for 30 cycles: 30 sec at 95° C., 30 sec at 50° C., 1 min at 72° C.; final step: 5 min at 72° C.

The amplified DNA fragment was purified by agarose gel-electrophoresis, extracted using "GenElute Spin Columns" ("Sigma", USA) and precipitated by ethanol. The obtained DNA fragment was used for electroporation and Red-mediated integration into the bacterial chromosome of the *E. coli* MG1655 ΔtyrR ΔpheA::cat tyrA-ssrA/pKD46 as described previously. The resulting *E. coli* strains MG1655 ΔtyrR tyrA-ssrA/pKD46 were selected on the minimal medium M9. The absence of L-phenylalanine in the medium enabled the selection of colonies that were Phe⁺ with prototrophic properties.

4. Verification of the pheA Gene Reconstruction by PCR

After 24 h of growth, colonies were tested for the presence of pheA gene by PCR using locus-specific primers P4 (SEQ ID NO: 12) and P5 (SEQ ID NO: 13). For this purpose, a freshly isolated colony was suspended in water (20 μl)and 1 μl of the obtained suspension was used for PCR. The temperature profile was as follows: the initial DNA denaturation at 95° C. for 5 min; then 30 cycles (denaturation at 95° C. for 30 s, annealing at 50° C. for 30 s, and elongation at 72° C. for 1 min 10 sec), and a final elongation at 72° C. for 5 min.

A few of the Phe+ colonies tested contained the required 1827-bp DNA fragment, confirming the substitution of the 2373-bp region of the cat gene by the pheA gene (see FIG. 2). The resulting mutant strain was named MG1655 ΔtyrR tyrA-ssrA/pKD46 (FIG. 4).

Then, to eliminate the pKD46 plasmid, two passages on L-agar with Cm at 42° C. were performed and the colonies which appeared were tested for sensitivity to ampicillin.

Thus, a strain with the mutant tyrA gene and missing the tyrR gene was obtained. This strain was named MG1655ΔtyrRtyrA-ssrA.

Example 2

Effect of ssrA Tagging of tyrA Gene on the L-phenylalanine Production

Then E. coli strains MG1655 ΔtyrR tyrA-ssrA and MG1655 ΔtyrR were each cultivated at 37° C. for 18 hours in a nutrient broth, and 0.3 ml of each of these cultures was inoculated into 3 ml of fermentation medium having the following composition in a 20×200 mm test tube and cultivated at 32° C. for 72 hours with a rotary shaker.

After cultivation, the accumulated amounts of L-phenylalanine and L-tyrosine in the medium were determined by TLC. A thin-layer silica gel plate (10×15 cm) spotted with an aliquot (1-2 µl) of the culture broth was developed with a developing solvent (2-propanol:ethyl acetate:ammonia:water=16:16:3:9) and L-phenylalanine and L-tyrosine were detected with the ninhydrin reagent. The results of four tubes of fermentations are shown in Table 1.

The composition of the fermentation medium (g/l) was as follows:

| | |
|---|---|
| Glucose | 40.0 |
| (NH4)2SO4 | 16.0 |
| K2HPO4 | 1.0 |
| MgSO4•7H2O | 1.0 |
| MnSO4•5H2O | 0.01 |
| FeSO4•7H2O | 0.01 |
| Yeast extract | 2.0 |
| CaCO3 | 30.0 |

MgSO4•7H2O and CaCO3 were each sterilized separately.

It can be seen from Table 1 that MG1655 ΔtyrR tyrA-ssrA caused the accumulation of a higher amount of L-phenylalanine and a lower amount of L-tyrosine as compared with MG1655 ΔtyrR.

Example 3

Effect of ssrA Tagging of pgi Gene on the L-histidine Production

L-histidine-producing strains with the pgi gene tagged with peptides SEQ ID NO: 2 or SEQ ID NO: 15 were obtained. These two peptides differ by substitution of one of the terminal amino acid residues, either alanine or valine. These strains were obtained as follows. First, two variants of the pgi gene containing additional nucleotide sequences at the 3'-end of the gene coding for peptides SEQ ID NO: 2 or SEQ ID NO: 15 were obtained by PCR using chromosomal DNA of E. coli strain MG1655 and primers pgi 1 (SEQ ID NO: 16) and pgi-LAA (SEQ ID NO: 17) or pgiLVA (SEQ ID NO:18), respectively. Primer pgi 1 is complementary to the 5'end of pgi gene and contains the SadI restriction site at the 5'-end thereof. Primers pgi-LVA and pgi-LAA contain regions of the 3'-end of the pgi gene minus the stop-codon, a region encoding for the short peptides SEQ ID NO: 2 or SEQ ID NO: 15, respectively, a stop-codon, and the XbaI restriction site at the 5'-end thereof. Second, two PCR fragments were separately treated with SacI and XbaI restrictases and ligated into the pMW119 plasmid which had been previously treated with the same restrictases. The resulting plasmids were named pMW-pgi-ssrA$^{LAA}$ and pMWpgi-ssrA$^{LVA}$, respectively.

Then, the wild-type pgi gene was deleted in the L-histidine-producing strain 80.

For this purpose, the DNA fragment containing the Cm$^R$ marker encoded by the cat gene was obtained by PCR using primers P7 (SEQ ID NO: 19) and P8 (SEQ ID NO: 20), and plasmid pMW118-attL-Cm-attR as a template (WO 05/010175) (FIG. 2). Primer P7 contains both a region identical to the 36-nt region located at the 5' end of the pgi gene and a region complementary to the 28-nt attR region of pMW118-attL-Cm-attR. Primer P8 contains both a region identical to the 36-nt region located at the 3' end of the pgi gene and a region complementary to the 28-nt attL region of pMW118-attL-Cm-attR. PCR and electroporation of the obtained DNA fragment were performed as described above (see Example 1, section 1).

Deletion of the pgi gene was verified by PCR using locus-specific primers P9 (SEQ ID NO: 21) and P10 (SEQ ID NO: 22). For this purpose, a freshly isolated colony was suspended in water (20 µl) and 1 µl of this suspension was used for PCR. The temperature profile was as follows: the initial DNA denaturation at 95° C. for 5 min; then 30 cycles (denaturation at 95° C. for 30 s, annealing at 50° C. for 30 s, and elongation at 72° C. for 1 min 10 sec), and a final elongation at 72° C. for 5 min.

A few Cm$^R$ colonies tested contained the required 1709-bp DNA fragment confirming the substitution of the 1651-bp native region of the pgi gene by cat gene. The resulting mutant strain was named 80 Δpgi.

The obtained strain 80 Δpgi was transformed with the plasmids pMW-pgi-ssrA$^{LAA}$ and pMWpgi-ssrA$^{LVA}$ as described above. The resulting strains were named 80 Δpgi/pMW-pgi-ssrA$^{LAA}$ and 80 Δpgi/pMWpgi-ssrA$^{LVA}$, respectively.

For mini jar batch-fermentation, one loop of each strain 80, 80 Δpgi/pMW-pgi-ssrA$^{LAA}$ and 80 Δpgi/pMWpgi-ssrA$^{LVA}$ grown on L-agar was transferred to L-broth and cultivated at 30° C. with rotation (140 rpm) to reach an optical density of culture OD$_{540}$≈2.0. Then 25 ml of seed culture was added to 250 ml of medium for fermentation and cultivated at 29° C. for with rotation (1500 rpm). Duration of the batch-fermentation was approximately 35-40 hours. After the cultivation the amount of histidine which had accumulated in the medium was determined by paper chromatography. The paper was developed with a mobile phase: n-butanol:acetic acid:water=4:1:1 (v/v). A solution of ninhydrin (0.5%) in acetone was used as a visualizing reagent. The results are shown in Table 2. It can be seen from the Table 2 that strains 80 Δpgi/pMW-pgi-ssrA$^{LAA}$ and 80 Δpgi/pMWpgi-ssrA$^{LVA}$ caused the accumulation of a higher amount of L-histidine as compared with strain 80.

The composition of the fermentation medium (pH 6.0) (g/l):

| | |
|---|---|
| Glucose | 50.0 |
| Mameno | 0.2 of TN |
| (NH4)2SO4 | 8.0 |
| KH2PO4 | 0.5 |
| MgSO4 7H2O | 0.4 |
| FeSO4 7H2O | 0.02 |

| | |
|---|---|
| MnSO$_4$ | 0.02 |
| Thiamine | 0.001 |
| Betaine | 2.0 |
| L-proline | 0.8 |
| L-glutamate | 3.0 |
| L-aspartate | 1.0 |
| Adenosine | 0.2 |

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

TABLE 1

| Strain | OD$_{540}$ | Phe, g/l | Tyr, g/l |
|---|---|---|---|
| MG1655ΔtyrR | 28.5 ± 0.6 | 0.13 ± 0.01 | 0.017 ± 0.002 |
| MG1655ΔtyrR tyrA-ssrA | 26.3 ± 0.4 | 0.46 ± 0.04 | traces |

TABLE 2

| Strain | OD$_{450}$ | Amount of histidine, g/l | Yield per glucose, % |
|---|---|---|---|
| 80 (VKPM B-7270) | 31.0 | 9.0 | 18.0 |
| 80 Δpgi | 20.2 | 8.1 | 16.2 |
| 80 Δpgi/pMW-pgi-ssrA$^{LAA}$ | 23.2 | 10.7 | 21.4 |
| 80 Δpgi/pMW-pgi-ssrA$^{LVA}$ | 22.8 | 10.6 | 21.2 |

We claim:

1. A method for producing a lower alkyl ester of α-L-aspartyl-L-phenylalanine, comprising:
    A) cultivating a bacterium of *Escherichia coli* in a culture medium which is able to produce and accumulate L-phenylalanine in the medium, and
    B) synthesizing the lower alkyl ester of α-L-aspartyl-L-phenylalanine from aspartic acid or a derivative thereof and the L-phenylalanine obtained in step A);
    wherein the bacterium comprises a DNA comprising:
    i) a gene selected from the group consisting of tyrA, pheA, pgi, ilvE, ilvA, tdcB, sdaA, sdaB, argA, argG, proB, thrB, and combinations thereof, and
    ii) a DNA fragment able to be transcribed and encoding the peptide of SEQ ID NO: 2, or a variant thereof consisting of a deletion, insertion, substitution, or addition of 1 amino acid as compared to SEQ ID NO: 2; and
    wherein said DNA fragment of ii) is attached to the 3' end of said gene of i) and consequently enhances production of an L-amino acid.

2. The method according to claim 1, wherein said bacterium is an L-phenylalanine producing bacterium.

3. The method according to claim 1, wherein said gene is tyrA, which encodes the bifunctional enzyme chorismate mutase/prephenate dehydrogenase.

4. The method according to claim 1, wherein said bacterium is an L-histidine-producing bacterium.

5. The method according to claim 1, wherein said gene is pgi which encodes a phosphoglucose isomerase enzyme.

6. The method according to claim 1, wherein the variant is the peptide of SEQ ID NO: 15.

7. The method according to claim 1, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride,
    E) separating the lower alkyl ester of N-acyl-α-L-aspartyl-L-phenylalanine from the condensation reaction mixture, and
    F) hydrogenating the lower alkyl ester of N-acyl-α-L-aspartyl-L-phenylalanine to generate the lower alkyl ester of α-L-aspartyl-L-phenylalanine.

8. The method according to claim 2, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride,
    E) separating the lower alkyl ester of N-acyl-α-L-aspartyl-L-phenylalanine from the condensation reaction mixture, and
    F) hydrogenating the lower alkyl ester of N-acyl-α-L-aspartyl-L-phenylalanine to generate the lower alkyl ester of α-L-aspartyl-L-phenylalanine.

9. The method according to claim 3, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride,
    E) separating the lower alkyl ester of N-acyl-α-L-aspartyl-L-phenylalanine from the condensation reaction mixture, and
    F) hydrogenating the lower alkyl ester of N-acyl-α-L-aspartyl-L-phenylalanine to generate the lower alkyl ester of α-L-aspartyl-L-phenylalanine.

10. The method according to claim 4, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride,
    E) separating the lower alkyl ester of N-acyl-α-L-aspartyl-L-phenylalanine from the condensation reaction mixture, and
    F) hydrogenating the lower alkyl ester of N-acyl-α-L-aspartyl-L-phenylalanine to generate the lower alkyl ester of α-L-aspartyl-L-phenylalanine.

11. The method according to claim 5, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride,
    E) separating the lower alkyl ester of N-acyl-α-L-aspartyl-L-phenylalanine from the condensation reaction mixture, and
    F) hydrogenating the lower alkyl ester of N-acyl-α-L-aspartyl-L-phenylalanine to generate the lower alkyl ester of α-L-aspartyl-L-phenylalanine.

12. The method according to claim 6, wherein said synthesizing in step B) further comprises:
    C) esterifying the L-phenylalanine to generate a lower alkyl ester of L-phenylalanine,
    D) condensing the lower alkyl ester of L-phenylalanine with the aspartic acid derivative in a condensation reaction mixture, wherein the derivative is N-acyl-L-aspartic anhydride, E) separating the lower alkyl ester of N-acyl-α-L-aspartyl-L-phenylalanine from the condensation reaction mixture, and
F) hydrogenating the lower alkyl ester of N-acyl-α-L-aspartyl-L-phenylalanine to generate the lower alkyl ester of α-L-aspartyl-L-phenylalanine.

\* \* \* \* \*

SEQUENCE LISTING

<160> NUMBER OF SEQ ID NOS: 29

<210> SEQ ID NO 1
<211> LENGTH: 363
<212> TYPE: DNA
<213> ORGANISM: Escherichia coli

<400> SEQUENCE: 1

```
ggggctgatt ctggattcga cgggatttgc gaaacccaag gtgcatgccg aggggcggtt      60
ggcctcgtaa aaagccgcaa aaaatagtcg caaacgacga aaactacgct ttagcagctt     120
aataacctgc ttagagccct ctctccctag cctccgctct taggacgggg atcaagagag     180
gtcaaaccca aaagagatcg cgtggaagcc ctgcctgggg ttgaagcgtt aaaacttaat     240
caggctagtt tgttagtggc gtgtccgtcc gcagctggca agcgaatgta aagactgact     300
aagcatgtag taccgaggat gtaggaattt cggacgcggg ttcaactccc gccagctcca     360
cca                                                                    363
```

<210> SEQ ID NO 2
<211> LENGTH: 11
<212> TYPE: PRT
<213> ORGANISM: Escherichia coli

<400> SEQUENCE: 2

```
Ala Ala Asn Asp Glu Asn Tyr Ala Leu Ala Ala
1               5                   10
```

<210> SEQ ID NO 3
<211> LENGTH: 1122
<212> TYPE: DNA
<213> ORGANISM: Escherichia coli
<220> FEATURE:
<221> NAME/KEY: CDS
<222> LOCATION: (1)..(1122)
<223> OTHER INFORMATION: tyrA

<400> SEQUENCE: 3

```
atg gtt gct gaa ttg acc gca tta cgc gat caa att gat gaa gtc gat        48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa        96
Lys Ala Leu Leu Asn Leu Leu Ala Lys Arg Leu Glu Leu Val Ala Glu
                20                  25                  30
```

-continued

| | | |
|---|---|---|
| gtg ggc gag gtg aaa agc cgc ttt gga ctg cct att tat gtt ccg gag<br>Val Gly Glu Val Lys Ser Arg Phe Gly Leu Pro Ile Tyr Val Pro Glu<br>35 40 45 | | 144 |
| cgc gag gca tct atg ttg gcc tcg cgt cgt gca gag gcg gaa gct ctg<br>Arg Glu Ala Ser Met Leu Ala Ser Arg Arg Ala Glu Ala Glu Ala Leu<br>50 55 60 | | 192 |
| ggt gta ccg cca gat ctg att gag gat gtt ttg cgt cgg gtg atg cgt<br>Gly Val Pro Pro Asp Leu Ile Glu Asp Val Leu Arg Arg Val Met Arg<br>65 70 75 80 | | 240 |
| gaa tct tac tcc agt gaa aac gac aaa gga ttt aaa aca ctt tgt ccg<br>Glu Ser Tyr Ser Ser Glu Asn Asp Lys Gly Phe Lys Thr Leu Cys Pro<br>85 90 95 | | 288 |
| tca ctg cgt ccg gtg gtt atc gtc ggc ggt ggc ggt cag atg gga cgc<br>Ser Leu Arg Pro Val Val Ile Val Gly Gly Gly Gly Gln Met Gly Arg<br>100 105 110 | | 336 |
| ctg ttc gag aag atg ctg acc ctc tcg ggt tat cag gtg cgg att ctg<br>Leu Phe Glu Lys Met Leu Thr Leu Ser Gly Tyr Gln Val Arg Ile Leu<br>115 120 125 | | 384 |
| gag caa cat gac tgg gat cga gcg gct gat att gtt gcc gat gcc gga<br>Glu Gln His Asp Trp Asp Arg Ala Ala Asp Ile Val Ala Asp Ala Gly<br>130 135 140 | | 432 |
| atg gtg att gtt agt gtg cca atc cac gtt act gag caa gtt att ggc<br>Met Val Ile Val Ser Val Pro Ile His Val Thr Glu Gln Val Ile Gly<br>145 150 155 160 | | 480 |
| aaa tta ccg cct tta ccg aaa gat tgt att ctg gtc gat ctg gca tca<br>Lys Leu Pro Pro Leu Pro Lys Asp Cys Ile Leu Val Asp Leu Ala Ser<br>165 170 175 | | 528 |
| gtg aaa aat ggg cca tta cag gcc atg ctg gtg gcg cat gat ggt ccg<br>Val Lys Asn Gly Pro Leu Gln Ala Met Leu Val Ala His Asp Gly Pro<br>180 185 190 | | 576 |
| gtg ctg ggg cta cac ccg atg ttc ggt ccg gac agc ggt agc ctg gca<br>Val Leu Gly Leu His Pro Met Phe Gly Pro Asp Ser Gly Ser Leu Ala<br>195 200 205 | | 624 |
| aag caa gtt gtg gtc tgg tgt gat gga cgt aaa ccg gaa gca tac caa<br>Lys Gln Val Val Val Trp Cys Asp Gly Arg Lys Pro Glu Ala Tyr Gln<br>210 215 220 | | 672 |
| tgg ttt ctg gag caa att cag gtc tgg ggc gct cgg ctg cat cgt att<br>Trp Phe Leu Glu Gln Ile Gln Val Trp Gly Ala Arg Leu His Arg Ile<br>225 230 235 240 | | 720 |
| agc gcc gtc gag cac gat cag aat atg gcg ttt att cag gca ctg cgc<br>Ser Ala Val Glu His Asp Gln Asn Met Ala Phe Ile Gln Ala Leu Arg<br>245 250 255 | | 768 |
| cac ttt gct act ttt gct tac ggg ctg cac ctg gca gaa gaa aat gtt<br>His Phe Ala Thr Phe Ala Tyr Gly Leu His Leu Ala Glu Glu Asn Val<br>260 265 270 | | 816 |
| cag ctt gag caa ctt ctg gcg ctc tct tcg ccg att tac cgc ctt gag<br>Gln Leu Glu Gln Leu Leu Ala Leu Ser Ser Pro Ile Tyr Arg Leu Glu<br>275 280 285 | | 864 |
| ctg gcg atg gtc ggg cga ctg ttt gct cag gat ccg cag ctt tat gcc<br>Leu Ala Met Val Gly Arg Leu Phe Ala Gln Asp Pro Gln Leu Tyr Ala<br>290 295 300 | | 912 |
| gac atc att atg tcg tca gag cgt aat ctg gcg tta atc aaa cgt tac<br>Asp Ile Ile Met Ser Ser Glu Arg Asn Leu Ala Leu Ile Lys Arg Tyr<br>305 310 315 320 | | 960 |
| tat aag cgt ttc ggc gag gcg att gag ttg ctg gag cag ggc gat aag<br>Tyr Lys Arg Phe Gly Glu Ala Ile Glu Leu Leu Glu Gln Gly Asp Lys<br>325 330 335 | | 1008 |
| cag gcg ttt att gac agt ttc cgc aag gtg gag cac tgg ttc ggc gat<br>Gln Ala Phe Ile Asp Ser Phe Arg Lys Val Glu His Trp Phe Gly Asp<br>340 345 350 | | 1056 |

```
tac gca cag cgt ttt cag agt gaa agc cgt gtg tta ttg cgt cag gcg     1104
Tyr Ala Gln Arg Phe Gln Ser Glu Ser Arg Val Leu Leu Arg Gln Ala
        355                 360                 365 aat gac aat cgc cag taa                                              1122
Asn Asp Asn Arg Gln
        370

<210> SEQ ID NO 4
<211> LENGTH: 373
<212> TYPE: PRT
<213> ORGANISM: Escherichia coli

<400> SEQUENCE: 4

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Gly Gly Gly Gln Met Gly Arg
            100                 105                 110

Leu Phe Glu Lys Met Leu Thr Leu Ser Gly Tyr Gln Val Arg Ile Leu
            115                 120                 125

Glu Gln His Asp Trp Asp Arg Ala Ala Asp Ile Val Ala Asp Ala Gly
        130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335
```

```
Gln Ala Phe Ile Asp Ser Phe Arg Lys Val Glu His Trp Phe Gly Asp
                340                 345                 350

Tyr Ala Gln Arg Phe Gln Ser Glu Ser Arg Val Leu Leu Arg Gln Ala
            355                 360                 365

Asn Asp Asn Arg Gln
        370

<210> SEQ ID NO 5
<211> LENGTH: 1161
<212> TYPE: DNA
<213> ORGANISM: Escherichia coli
<220> FEATURE:
<221> NAME/KEY: CDS
<222> LOCATION: (1)..(1161)
<223> OTHER INFORMATION: pheA

<400> SEQUENCE: 5
```

| | | | | | | | | | | | | | | | | |
|---|---|---|---|---|---|---|---|---|---|---|---|---|---|---|---|---|
| atg | aca | tcg | gaa | aac | ccg | tta | ctg | gcg | ctg | cga | gag | aaa | atc | agc | gcg | 48 |
| Met | Thr | Ser | Glu | Asn | Pro | Leu | Leu | Ala | Leu | Arg | Glu | Lys | Ile | Ser | Ala | |
| 1 | | | | 5 | | | | | 10 | | | | | 15 | | |
| ctg | gat | gaa | aaa | tta | tta | gcg | tta | ctg | gca | gaa | cgg | cgc | gaa | ctg | gcc | 96 |
| Leu | Asp | Glu | Lys | Leu | Leu | Ala | Leu | Leu | Ala | Glu | Arg | Arg | Glu | Leu | Ala | |
| | | | 20 | | | | | 25 | | | | | 30 | | | |
| gtc | gag | gtg | gga | aaa | gcc | aaa | ctg | ctc | tcg | cat | cgc | ccg | gta | cgt | gat | 144 |
| Val | Glu | Val | Gly | Lys | Ala | Lys | Leu | Leu | Ser | His | Arg | Pro | Val | Arg | Asp | |
| | | 35 | | | | | 40 | | | | | 45 | | | | |
| att | gat | cgt | gaa | cgc | gat | ttg | ctg | gaa | aga | tta | att | acg | ctc | ggt | aaa | 192 |
| Ile | Asp | Arg | Glu | Arg | Asp | Leu | Leu | Glu | Arg | Leu | Ile | Thr | Leu | Gly | Lys | |
| | 50 | | | | | 55 | | | | | 60 | | | | | |
| gcg | cac | cat | ctg | gac | gcc | cat | tac | att | act | cgc | ctg | ttc | cag | ctc | atc | 240 |
| Ala | His | His | Leu | Asp | Ala | His | Tyr | Ile | Thr | Arg | Leu | Phe | Gln | Leu | Ile | |
| 65 | | | | | 70 | | | | | 75 | | | | | 80 | |
| att | gaa | gat | tcc | gta | tta | act | cag | cag | gct | ttg | ctc | caa | caa | cat | ctc | 288 |
| Ile | Glu | Asp | Ser | Val | Leu | Thr | Gln | Gln | Ala | Leu | Leu | Gln | Gln | His | Leu | |
| | | | | 85 | | | | | 90 | | | | | 95 | | |
| aat | aaa | att | aat | ccg | cac | tca | gca | cgc | atc | gct | ttt | ctc | ggc | ccc | aaa | 336 |
| Asn | Lys | Ile | Asn | Pro | His | Ser | Ala | Arg | Ile | Ala | Phe | Leu | Gly | Pro | Lys | |
| | | | 100 | | | | | 105 | | | | | 110 | | | |
| ggt | tct | tat | tcc | cat | ctt | gcg | gcg | cgc | cag | tat | gct | gcc | cgt | cac | ttt | 384 |
| Gly | Ser | Tyr | Ser | His | Leu | Ala | Ala | Arg | Gln | Tyr | Ala | Ala | Arg | His | Phe | |
| | | 115 | | | | | 120 | | | | | 125 | | | | |
| gag | caa | ttc | att | gaa | agt | ggc | tgc | gcc | aaa | ttt | gcc | gat | att | ttt | aat | 432 |
| Glu | Gln | Phe | Ile | Glu | Ser | Gly | Cys | Ala | Lys | Phe | Ala | Asp | Ile | Phe | Asn | |
| | 130 | | | | | 135 | | | | | 140 | | | | | |
| cag | gtg | gaa | acc | ggc | cag | gcc | gac | tat | gcc | gtc | gta | ccg | att | gaa | aat | 480 |
| Gln | Val | Glu | Thr | Gly | Gln | Ala | Asp | Tyr | Ala | Val | Val | Pro | Ile | Glu | Asn | |
| 145 | | | | | 150 | | | | | 155 | | | | | 160 | |
| acc | agc | tcc | ggt | gcc | ata | aac | gac | gtt | tac | gat | ctg | ctg | caa | cat | acc | 528 |
| Thr | Ser | Ser | Gly | Ala | Ile | Asn | Asp | Val | Tyr | Asp | Leu | Leu | Gln | His | Thr | |
| | | | | 165 | | | | | 170 | | | | | 175 | | |
| agc | ttg | tcg | att | gtt | ggc | gag | atg | acg | tta | act | atc | gac | cat | tgt | ttg | 576 |
| Ser | Leu | Ser | Ile | Val | Gly | Glu | Met | Thr | Leu | Thr | Ile | Asp | His | Cys | Leu | |
| | | | 180 | | | | | 185 | | | | | 190 | | | |
| ttg | gtc | tcc | ggc | act | act | gat | tta | tcc | acc | atc | aat | acg | gtc | tac | agc | 624 |
| Leu | Val | Ser | Gly | Thr | Thr | Asp | Leu | Ser | Thr | Ile | Asn | Thr | Val | Tyr | Ser | |
| | | 195 | | | | | 200 | | | | | 205 | | | | |
| cat | ccg | cag | cca | ttc | cag | caa | tgc | agc | aaa | ttc | ctt | aat | cgt | tat | ccg | 672 |
| His | Pro | Gln | Pro | Phe | Gln | Gln | Cys | Ser | Lys | Phe | Leu | Asn | Arg | Tyr | Pro | |
| | 210 | | | | | 215 | | | | | 220 | | | | | |
| cac | tgg | aag | att | gaa | tat | acc | gaa | agt | acg | tct | gcg | gca | atg | gaa | aag | 720 |
| His | Trp | Lys | Ile | Glu | Tyr | Thr | Glu | Ser | Thr | Ser | Ala | Ala | Met | Glu | Lys | |

```
                225                 230                 235                 240 gtt gca cag gca aaa tca ccg cat gtt gct gcg ttg gga agc gaa gct     768
Val Ala Gln Ala Lys Ser Pro His Val Ala Ala Leu Gly Ser Glu Ala
                245                 250                 255 ggc ggc act ttg tac ggt ttg cag gta ctg gag cgt att gaa gca aat     816
Gly Gly Thr Leu Tyr Gly Leu Gln Val Leu Glu Arg Ile Glu Ala Asn
            260                 265                 270 cag cga caa aac ttc acc cga ttt gtg gtg ttg gcg cgt aaa gcc att     864
Gln Arg Gln Asn Phe Thr Arg Phe Val Val Leu Ala Arg Lys Ala Ile
        275                 280                 285 aac gtg tct gat cag gtt ccg gcg aaa acc acg ttg tta atg gcg acc     912
Asn Val Ser Asp Gln Val Pro Ala Lys Thr Thr Leu Leu Met Ala Thr
    290                 295                 300 ggg caa caa gcc ggt gcg ctg gtt gaa gcg ttg ctg gta ctg cgc aac     960
Gly Gln Gln Ala Gly Ala Leu Val Glu Ala Leu Leu Val Leu Arg Asn
305                 310                 315                 320 cac aat ctg att atg acc cgt ctg gaa tca cgc ccg att cac ggt aat    1008
His Asn Leu Ile Met Thr Arg Leu Glu Ser Arg Pro Ile His Gly Asn
                325                 330                 335 cca tgg gaa gag atg ttc tat ctg gat att cag gcc aat ctt gaa tca    1056
Pro Trp Glu Glu Met Phe Tyr Leu Asp Ile Gln Ala Asn Leu Glu Ser
            340                 345                 350 gcg gaa atg caa aaa gca ttg aaa gag tta ggg gaa atc acc cgt tca    1104
Ala Glu Met Gln Lys Ala Leu Lys Glu Leu Gly Glu Ile Thr Arg Ser
        355                 360                 365 atg aag gta ttg ggc tgt tac cca agt gag aac gta gtg cct gtt gat    1152
Met Lys Val Leu Gly Cys Tyr Pro Ser Glu Asn Val Val Pro Val Asp
    370                 375                 380 cca acc tga                                                        1161
Pro Thr
385

<210> SEQ ID NO 6
<211> LENGTH: 386
<212> TYPE: PRT
<213> ORGANISM: Escherichia coli

<400> SEQUENCE: 6

Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160
```

```
Thr Ser Ser Gly Ala Ile Asn Asp Val Tyr Asp Leu Leu Gln His Thr
            165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
            195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Leu Ala Arg Lys Ala Ile
            275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
            340                 345                 350

Ala Glu Met Gln Lys Ala Leu Lys Glu Leu Gly Glu Ile Thr Arg Ser
            355                 360                 365

Met Lys Val Leu Gly Cys Tyr Pro Ser Glu Asn Val Val Pro Val Asp
370                 375                 380

Pro Thr
385

<210> SEQ ID NO 7
<211> LENGTH: 1650
<212> TYPE: DNA
<213> ORGANISM: Escherichia coli
<220> FEATURE:
<221> NAME/KEY: CDS
<222> LOCATION: (1)..(1650)

<400> SEQUENCE: 7 atg aaa aac atc aat cca acg cag acc gct gcc tgg cag gca cta cag     48
Met Lys Asn Ile Asn Pro Thr Gln Thr Ala Ala Trp Gln Ala Leu Gln
1               5                   10                  15 aaa cac ttc gat gaa atg aaa gac gtt acg atc gcc gat ctt ttt gct    96
Lys His Phe Asp Glu Met Lys Asp Val Thr Ile Ala Asp Leu Phe Ala
                20                  25                  30 aaa gac ggc gat cgt ttt tct aag ttc tcc gca acc ttc gac gat cag   144
Lys Asp Gly Asp Arg Phe Ser Lys Phe Ser Ala Thr Phe Asp Asp Gln
            35                  40                  45 atg ctg gtg gat tac tcc aaa aac cgc atc act gaa gag acg ctg gcg   192
Met Leu Val Asp Tyr Ser Lys Asn Arg Ile Thr Glu Glu Thr Leu Ala
        50                  55                  60 aaa tta cag gat ctg gcg aaa gag tgc gat ctg gcg ggc gcg att aag   240
Lys Leu Gln Asp Leu Ala Lys Glu Cys Asp Leu Ala Gly Ala Ile Lys
65                  70                  75                  80 tcg atg ttc tct ggc gag aag atc aac cgc act gaa aac cgc gcc gtg   288
Ser Met Phe Ser Gly Glu Lys Ile Asn Arg Thr Glu Asn Arg Ala Val
                85                  90                  95
```

```
                        85                  90                    95
ctg cac gta gcg ctg cgt aac cgt agc aat acc ccg att ttg gtt gat       336
Leu His Val Ala Leu Arg Asn Arg Ser Asn Thr Pro Ile Leu Val Asp
            100                 105                 110 ggc aaa gac gta atg ccg gaa gtc aac gcg gtg ctg gag aag atg aaa       384
Gly Lys Asp Val Met Pro Glu Val Asn Ala Val Leu Glu Lys Met Lys
        115                 120                 125 acc ttc tca gaa gcg att att tcc ggt gag tgg aaa ggt tat acc ggc       432
Thr Phe Ser Glu Ala Ile Ile Ser Gly Glu Trp Lys Gly Tyr Thr Gly
130                 135                 140 aaa gca atc act gac gta gtg aac atc ggg atc ggc ggt tct gac ctc       480
Lys Ala Ile Thr Asp Val Val Asn Ile Gly Ile Gly Gly Ser Asp Leu
145                 150                 155                 160 ggc cca tac atg gtg acc gaa gct ctg cgt ccg tac aaa aac cac ctg       528
Gly Pro Tyr Met Val Thr Glu Ala Leu Arg Pro Tyr Lys Asn His Leu
            165                 170                 175 aac atg cac ttt gtt tct aac gtc gat ggg act cac atc gcg gaa gtg       576
Asn Met His Phe Val Ser Asn Val Asp Gly Thr His Ile Ala Glu Val
        180                 185                 190 ctg aaa aaa gta aac ccg gaa acc acg ctg ttc ttg gta gca tct aaa       624
Leu Lys Lys Val Asn Pro Glu Thr Thr Leu Phe Leu Val Ala Ser Lys
    195                 200                 205 acc ttc acc act cag gaa act atg acc aac gcc cat agc gcg cgt gac       672
Thr Phe Thr Thr Gln Glu Thr Met Thr Asn Ala His Ser Ala Arg Asp
210                 215                 220 tgg ttc ctg aaa gcg gca ggt gat gaa aaa cac gtt gca aaa cac ttt       720
Trp Phe Leu Lys Ala Ala Gly Asp Glu Lys His Val Ala Lys His Phe
225                 230                 235                 240 gcg gcg ctt tcc acc aat gcc aaa gcc gtt ggc gag ttt ggt att gat       768
Ala Ala Leu Ser Thr Asn Ala Lys Ala Val Gly Glu Phe Gly Ile Asp
            245                 250                 255 act gcc aac atg ttc gag ttc tgg gac tgg gtt ggc ggc cgt tac tct       816
Thr Ala Asn Met Phe Glu Phe Trp Asp Trp Val Gly Gly Arg Tyr Ser
        260                 265                 270 ttg tgg tca gcg att ggc ctg tcg att gtt ctc tcc atc ggc ttt gat       864
Leu Trp Ser Ala Ile Gly Leu Ser Ile Val Leu Ser Ile Gly Phe Asp
    275                 280                 285 aac ttc gtt gaa ctg ctt tcc ggc gca cac gcg atg gac aag cat ttc       912
Asn Phe Val Glu Leu Leu Ser Gly Ala His Ala Met Asp Lys His Phe
290                 295                 300 tcc acc acg cct gcc gag aaa aac ctg cct gta ctg ctg gcg ctg att       960
Ser Thr Thr Pro Ala Glu Lys Asn Leu Pro Val Leu Leu Ala Leu Ile
305                 310                 315                 320 ggc atc tgg tac aac aat ttc ttt ggt gcg gaa act gaa gcg att ctg      1008
Gly Ile Trp Tyr Asn Asn Phe Phe Gly Ala Glu Thr Glu Ala Ile Leu
            325                 330                 335 ccg tat gac cag tat atg cac cgt ttc gcg gcg tac ttc cag cag ggc      1056
Pro Tyr Asp Gln Tyr Met His Arg Phe Ala Ala Tyr Phe Gln Gln Gly
        340                 345                 350 aat atg gag tcc aac ggt aag tat gtt gac cgt aac ggt aac gtt gtg      1104
Asn Met Glu Ser Asn Gly Lys Tyr Val Asp Arg Asn Gly Asn Val Val
    355                 360                 365 gat tac cag act ggc ccg att atc tgg ggt gaa cca ggc act aac ggt      1152
Asp Tyr Gln Thr Gly Pro Ile Ile Trp Gly Glu Pro Gly Thr Asn Gly
370                 375                 380 cag cac gcg ttc tac cag ctg atc cac cag gga acc aaa atg gta ccg      1200
Gln His Ala Phe Tyr Gln Leu Ile His Gln Gly Thr Lys Met Val Pro
385                 390                 395                 400 tgc gat ttc atc gct ccg gct atc acc cat aac ccg ctc tct gat cat      1248
```

```
Cys Asp Phe Ile Ala Pro Ala Ile Thr His Asn Pro Leu Ser Asp His
                405                 410                 415 cac cag aaa ctg ctg tct aac ttc ttc gcc cag acc gaa gcg ctg gcg    1296
His Gln Lys Leu Leu Ser Asn Phe Phe Ala Gln Thr Glu Ala Leu Ala
        420                 425                 430 ttt ggt aaa tcc cgc gaa gtg gtt gag cag gaa tat cgt gat cag ggt    1344
Phe Gly Lys Ser Arg Glu Val Val Glu Gln Glu Tyr Arg Asp Gln Gly
    435                 440                 445 aaa gat ccg gca acg ctt gac tac gtg gtg ccg ttc aaa gta ttc gaa    1392
Lys Asp Pro Ala Thr Leu Asp Tyr Val Val Pro Phe Lys Val Phe Glu
450                 455                 460 ggt aac cgc ccg acc aac tcc atc ctg ctg cgt gaa atc act ccg ttc    1440
Gly Asn Arg Pro Thr Asn Ser Ile Leu Leu Arg Glu Ile Thr Pro Phe
465                 470                 475                 480 agc ctg ggt gcg ttg att gcg ctg tat gag cac aaa atc ttt act cag    1488
Ser Leu Gly Ala Leu Ile Ala Leu Tyr Glu His Lys Ile Phe Thr Gln
                485                 490                 495 ggc gtg atc ctg aac atc ttc acc ttc gac cag tgg ggc gtg gaa ctg    1536
Gly Val Ile Leu Asn Ile Phe Thr Phe Asp Gln Trp Gly Val Glu Leu
            500                 505                 510 ggt aaa cag ctg gcg aac cgt att ctg cca gag ctg aaa gat gat aaa    1584
Gly Lys Gln Leu Ala Asn Arg Ile Leu Pro Glu Leu Lys Asp Asp Lys
        515                 520                 525 gaa atc agc agc cac gat agc tcg acc aat ggt ctg att aac cgc tat    1632
Glu Ile Ser Ser His Asp Ser Ser Thr Asn Gly Leu Ile Asn Arg Tyr
    530                 535                 540 aaa gcg tgg cgc ggt taa                                             1650
Lys Ala Trp Arg Gly
545

<210> SEQ ID NO 8
<211> LENGTH: 549
<212> TYPE: PRT
<213> ORGANISM: Escherichia coli

<400> SEQUENCE: 8

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175
```

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
            195                 200                 205

Thr Phe Thr Thr Gln Glu Thr Met Thr Asn Ala His Ser Ala Arg Asp
            210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
            245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
            290                 295                 300

Ser Thr Thr Pro Ala Glu Lys Asn Leu Pro Val Leu Ala Leu Ile
305                 310                 315                 320

Gly Ile Trp Tyr Asn Asn Phe Phe Gly Ala Glu Thr Glu Ala Ile Leu
            325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
            370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
            405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
            435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
            485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
            515                 520                 525

Glu Ile Ser Ser His Asp Ser Ser Thr Asn Gly Leu Ile Asn Arg Tyr
            530                 535                 540

Lys Ala Trp Arg Gly
545

<210> SEQ ID NO 9
<211> LENGTH: 60
<212> TYPE: DNA
<213> ORGANISM: Artificial sequence
<220> FEATURE:

<223> OTHER INFORMATION: Synthesized

<400> SEQUENCE: 9
atgacatcgg aaacccgtt actggcgctg cgagagtgaa gcctgctttt ttatactaag    60

<210> SEQ ID NO 10
<211> LENGTH: 60
<212> TYPE: DNA
<213> ORGANISM: Artificial sequence
<220> FEATURE:
<223> OTHER INFORMATION: Synthesized

<400> SEQUENCE: 10
gcaaacgacg aaaactacgc tttagcagct taacgctcaa gttagtataa aaagctgaa    60

<210> SEQ ID NO 11
<211> LENGTH: 54
<212> TYPE: DNA
<213> ORGANISM: Artificial sequence
<220> FEATURE:
<223> OTHER INFORMATION: Synthesized

<400> SEQUENCE: 11
gcagtgttat tgcgtcaggc gaatgacaat cgccaggcaa acgacgaaaa ctac    54

<210> SEQ ID NO 12
<211> LENGTH: 19
<212> TYPE: DNA
<213> ORGANISM: Artificial sequence
<220> FEATURE:
<223> OTHER INFORMATION: Synthesized

<400> SEQUENCE: 12
atgaaacaca taccgtttt    19

<210> SEQ ID NO 13
<211> LENGTH: 20
<212> TYPE: DNA
<213> ORGANISM: Artificial sequence
<220> FEATURE:
<223> OTHER INFORMATION: Synthesized

<400> SEQUENCE: 13
gtccggacag cggtagcctg    20

<210> SEQ ID NO 14
<211> LENGTH: 55
<212> TYPE: DNA
<213> ORGANISM: Artificial sequence
<220> FEATURE:
<223> OTHER INFORMATION: Synthesized

<400> SEQUENCE: 14
caggcaaacg acgaaaacta cgctttagca gcttaatcag gttggatcaa caggc    55

<210> SEQ ID NO 15
<211> LENGTH: 11
<212> TYPE: PRT
<213> ORGANISM: Escherichia coli

<400> SEQUENCE: 15

Ala Ala Asn Asp Glu Asn Tyr Ala Leu Val Ala
1               5                   10

<210> SEQ ID NO 16

<211> LENGTH: 30
<212> TYPE: DNA
<213> ORGANISM: Artificial sequence
<220> FEATURE:
<223> OTHER INFORMATION: Synthesized

<400> SEQUENCE: 16
ctcgagctca gagcgatact tcgctactat                                     30

<210> SEQ ID NO 17
<211> LENGTH: 71
<212> TYPE: DNA
<213> ORGANISM: Artificial sequence
<220> FEATURE:
<223> OTHER INFORMATION: Synthesized

<400> SEQUENCE: 17
ctctctagaa ttaagctgct aaagcgtagt tttcgtcgtt tgctgcaggc ctaccgcgcc    60
acgctttata g                                                        71

<210> SEQ ID NO 18
<211> LENGTH: 71
<212> TYPE: DNA
<213> ORGANISM: Artificial sequence
<220> FEATURE:
<223> OTHER INFORMATION: Synthesized

<400> SEQUENCE: 18
ctctctagaa ttaagctact aaagcgtagt tttcgtcgtt tgctgcaggc ctaccgcgcc    60
acgctttata g                                                        71

<210> SEQ ID NO 19
<211> LENGTH: 64
<212> TYPE: DNA
<213> ORGANISM: Artificial sequence
<220> FEATURE:
<223> OTHER INFORMATION: Synthesized

<400> SEQUENCE: 19
aatgaaaaac atcaatccaa cgcagaccgc tgcctgcgct caagttagta taaaaagct    60 gaac                                                                64

<210> SEQ ID NO 20
<211> LENGTH: 64
<212> TYPE: DNA
<213> ORGANISM: Artificial sequence
<220> FEATURE:
<223> OTHER INFORMATION: Synthesized

<400> SEQUENCE: 20
ttaaccgcgc cacgctttat agcggttaat cagacctgaa gcctgctttt ttatactaag    60
ttgg                                                                64

<210> SEQ ID NO 21
<211> LENGTH: 25
<212> TYPE: DNA
<213> ORGANISM: Artificial sequence
<220> FEATURE:
<223> OTHER INFORMATION: Synthesized

<400> SEQUENCE: 21
aatgaaaaac atcaatccaa cgcag                                         25

```
<210> SEQ ID NO 22
<211> LENGTH: 22
<212> TYPE: DNA
<213> ORGANISM: Artificial sequence
<220> FEATURE:
<223> OTHER INFORMATION: Synthesized

<400> SEQUENCE: 22
ttaaccgcgc cacgctttat ag                                              22

<210> SEQ ID NO 23
<211> LENGTH: 14
<212> TYPE: PRT
<213> ORGANISM: Bacillus subtilis

<400> SEQUENCE: 23

Gly Lys Thr Asn Ser Phe Asn Gln Asn Val Ala Leu Ala Ala
1               5                   10

<210> SEQ ID NO 24
<211> LENGTH: 9
<212> TYPE: PRT
<213> ORGANISM: Bacillus stearothermophilus

<400> SEQUENCE: 24

Gly Lys Gln Asn Tyr Ala Leu Ala Ala
1               5

<210> SEQ ID NO 25
<211> LENGTH: 10
<212> TYPE: PRT
<213> ORGANISM: Serratia marcescens

<400> SEQUENCE: 25

Ala Asn Asp Glu Asn Tyr Ala Leu Ala Ala
1               5                   10

<210> SEQ ID NO 26
<211> LENGTH: 10
<212> TYPE: PRT
<213> ORGANISM: Escherichia coli

<400> SEQUENCE: 26

Ala Asn Asp Glu Asn Tyr Ala Leu Ala Ala
1               5                   10

<210> SEQ ID NO 27
<211> LENGTH: 13
<212> TYPE: PRT
<213> ORGANISM: Artificial sequence
<220> FEATURE:
<223> OTHER INFORMATION: Synthesized

<400> SEQUENCE: 27

Ala Asn Asp Glu Thr Tyr Gly Glu Tyr Ala Leu Ala Ala
1               5                   10

<210> SEQ ID NO 28
<211> LENGTH: 13
<212> TYPE: PRT
<213> ORGANISM: Pseudomonas chlororaphis

<400> SEQUENCE: 28

Ala Asn Asp Glu Thr Tyr Gly Glu Tyr Ala Leu Ala Ala
1               5                   10
```

```
<210> SEQ ID NO 29
<211> LENGTH: 15
<212> TYPE: PRT
<213> ORGANISM: Pseudomonas putida

<400> SEQUENCE: 29

Ala Asn Asp Glu Thr Tyr Gly Glu Glu Thr Tyr Ala Leu Ala Ala
1               5                   10                  15
```